(12) United States Patent
Keller

(10) Patent No.: US 10,285,855 B2
(45) Date of Patent: May 14, 2019

(54) CAPSULOTOMY DEVICE WITH SUCTION CUP COMPRESSION CHAMBER

(75) Inventor: Christopher Guild Keller, El Cerrito, CA (US)

(73) Assignee: Mynosys Cellular Devices, Inc., Fremont, CA (US)

( * ) Notice: Subject to any disclaimer, the term of this patent is extended or adjusted under 35 U.S.C. 154(b) by 219 days.

(21) Appl. No.: 14/237,029

(22) PCT Filed: Aug. 6, 2012

(86) PCT No.: PCT/US2012/049788
§ 371 (c)(1),
(2), (4) Date: Feb. 4, 2014

(87) PCT Pub. No.: WO2013/022854
PCT Pub. Date: Feb. 14, 2013

(65) Prior Publication Data
US 2014/0207137 A1    Jul. 24, 2014

Related U.S. Application Data
(60) Provisional application No. 61/515,358, filed on Aug. 5, 2011.

(51) Int. Cl.
| | | |
|---|---|---|
| A61F 9/007 | (2006.01) | |
| A61B 18/14 | (2006.01) | |
| A61B 18/12 | (2006.01) | |

(52) U.S. Cl.
CPC ........ *A61F 9/00754* (2013.01); *A61F 9/0079* (2013.01); *A61B 18/1402* (2013.01); *A61B 2018/1266* (2013.01)

(58) Field of Classification Search
CPC ........ A61F 9/00754; A61F 2009/00889; A61F 2009/00887; A61F 2009/0087; A61B 2018/142
See application file for complete search history.

(56) References Cited

U.S. PATENT DOCUMENTS

| | | | | |
|---|---|---|---|---|
| 6,506,176 B1* | 1/2003 | Mittelstein | .............. | A61F 9/013 604/107 |
| 8,137,344 B2* | 3/2012 | Jia | .......................... | A61B 18/14 606/45 |

(Continued)

FOREIGN PATENT DOCUMENTS

| | | | |
|---|---|---|---|
| WO | WO 2009/140414 A1 | 11/2009 | |
| WO | WO2009140414 | * | 11/2009 |

OTHER PUBLICATIONS

PCT International Search Report and Written Opinion, PCT/US2012/049788, dated Dec. 24, 2012, 14 Pages.

Primary Examiner — Ronald Hupczey, Jr.
Assistant Examiner — Bo Ouyang
(74) Attorney, Agent, or Firm — Fenwick & West LLP

(57) ABSTRACT

A surgical device and procedure are provided for smoothly and easily accessing tissue to perform microsurgery, including a capsulotomy of a lens capsule of an eye. The device includes a handpiece with a tip for insertion into an incision in the cornea of the eye. A sliding element is disposed within the handpiece and a suction cup is mounted to the sliding element. The sliding element can be translated to move the suction cup into and out of the handpiece. A compression mechanism associated with the suction cup and the handpiece compresses the suction cup for deployment through the tip of the handpiece. The suction cup can expand inside the anterior chamber into a cutting position on the lens capsule. A cutting element mounted to the suction cup is used to cut a portion of the lens capsule and to remove the portion from the eye.

20 Claims, 41 Drawing Sheets

(56) References Cited

U.S. PATENT DOCUMENTS

| | | |
|---|---|---|
| 8,162,931 B2 | 4/2012 | Ben-Nun |
| 8,235,978 B2 | 8/2012 | Ben-Nun |
| 8,657,813 B2 | 2/2014 | Ben-Nun et al. |
| 2004/0260254 A1* | 12/2004 | Neilson ................ A61F 9/0017 604/297 |
| 2007/0191862 A1* | 8/2007 | Ellis .................... A61F 9/00754 606/107 |
| 2009/0216225 A1* | 8/2009 | Ben-Nun ............. A61B 18/082 606/45 |
| 2011/0071524 A1* | 3/2011 | Keller ................. A61F 9/00736 606/45 |
| 2011/0118734 A1 | 5/2011 | Auld et al. |
| 2014/0074088 A1 | 3/2014 | Ben Nun et al. |

* cited by examiner

Fig 7A1
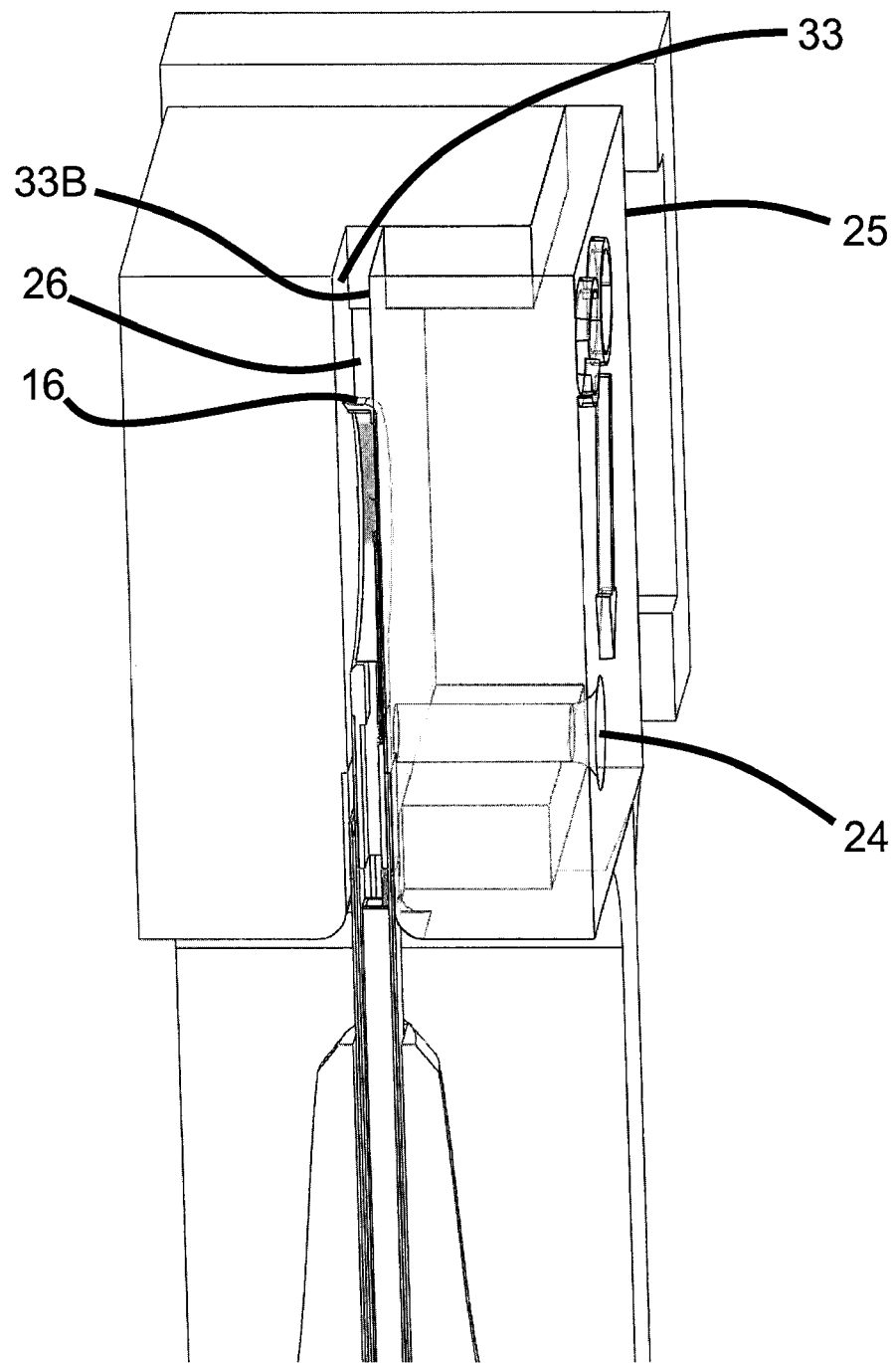

Fig. 7A2
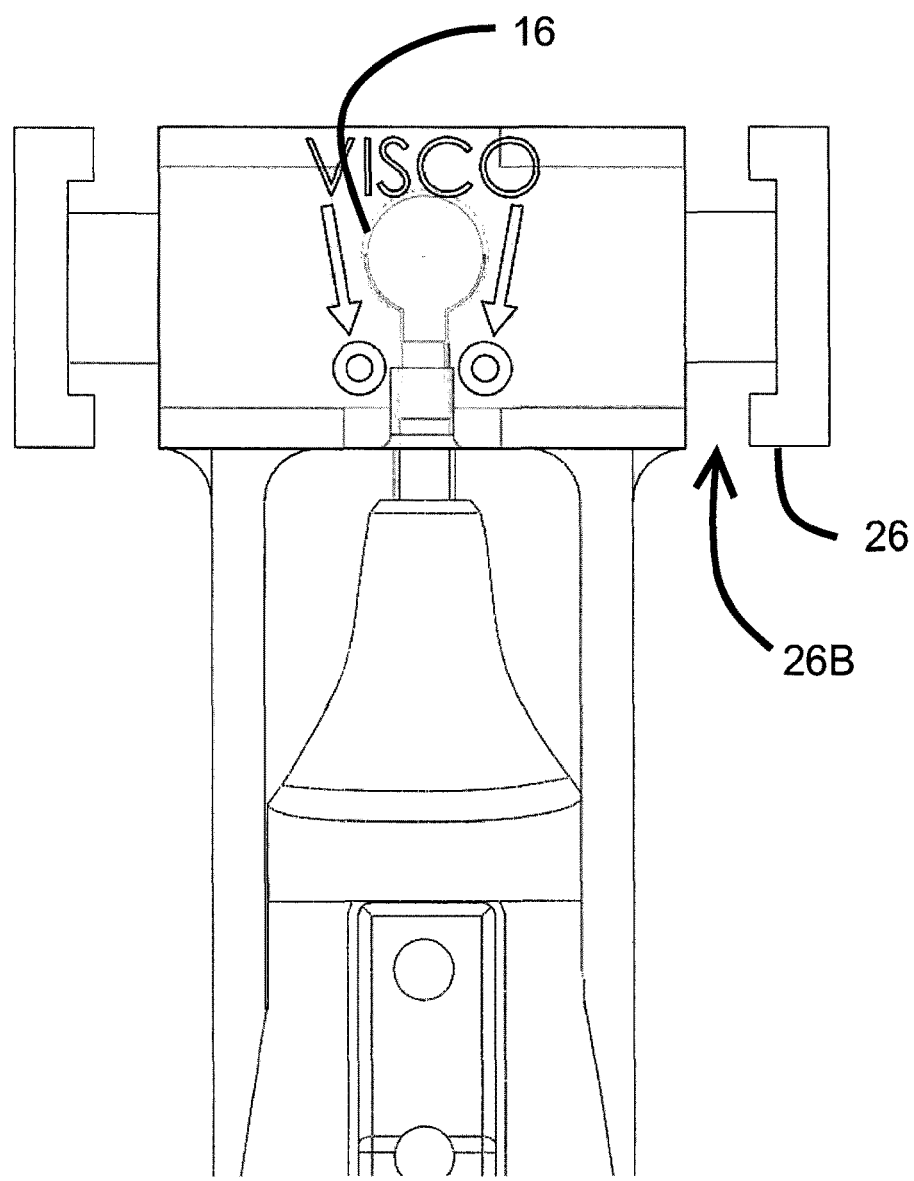

Fig. 7A3
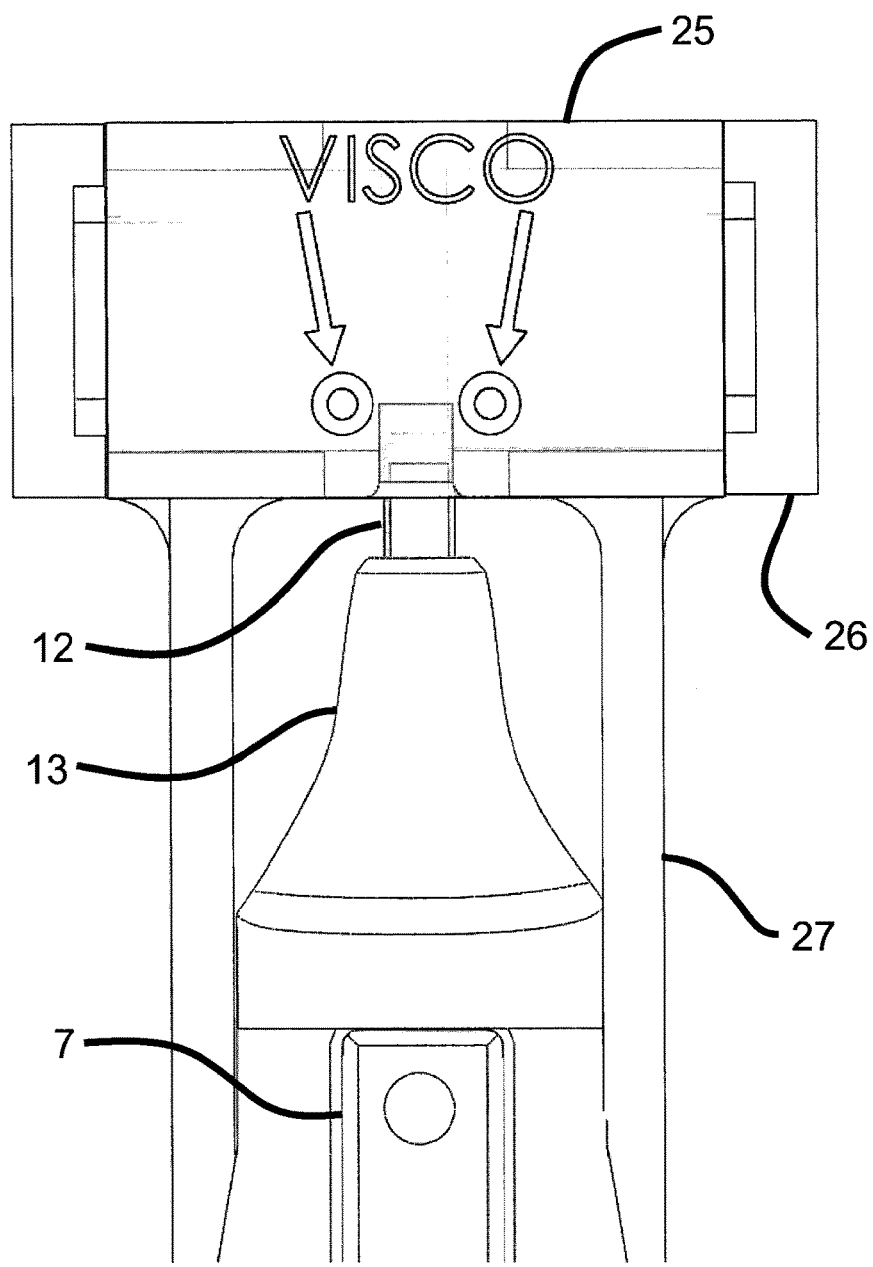

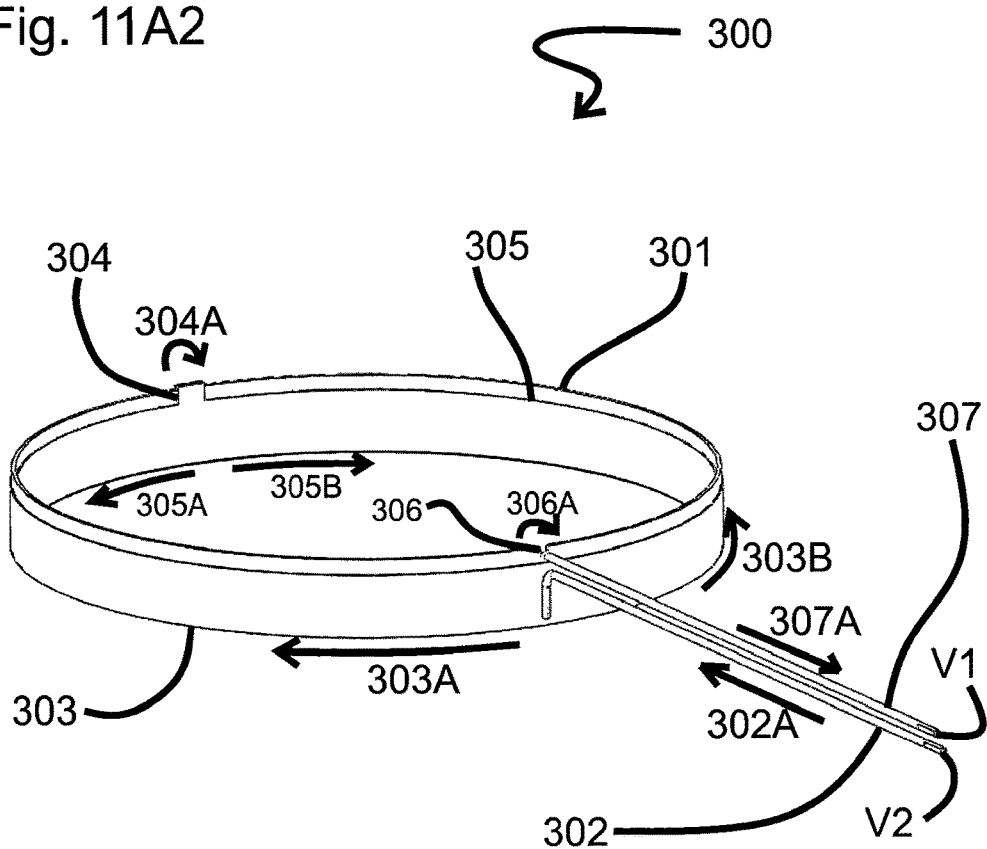
Fig. 11A2

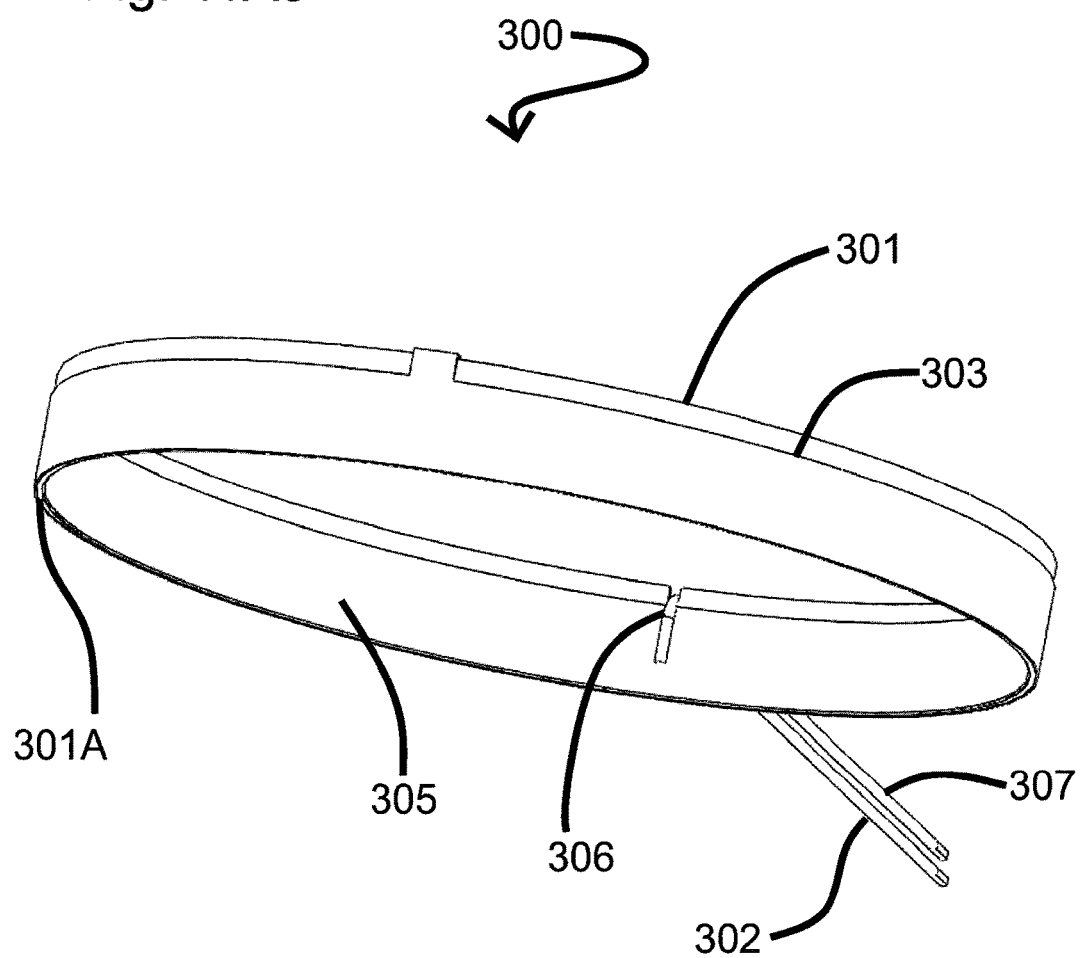
Fig. 11A3

Fig. 11A4
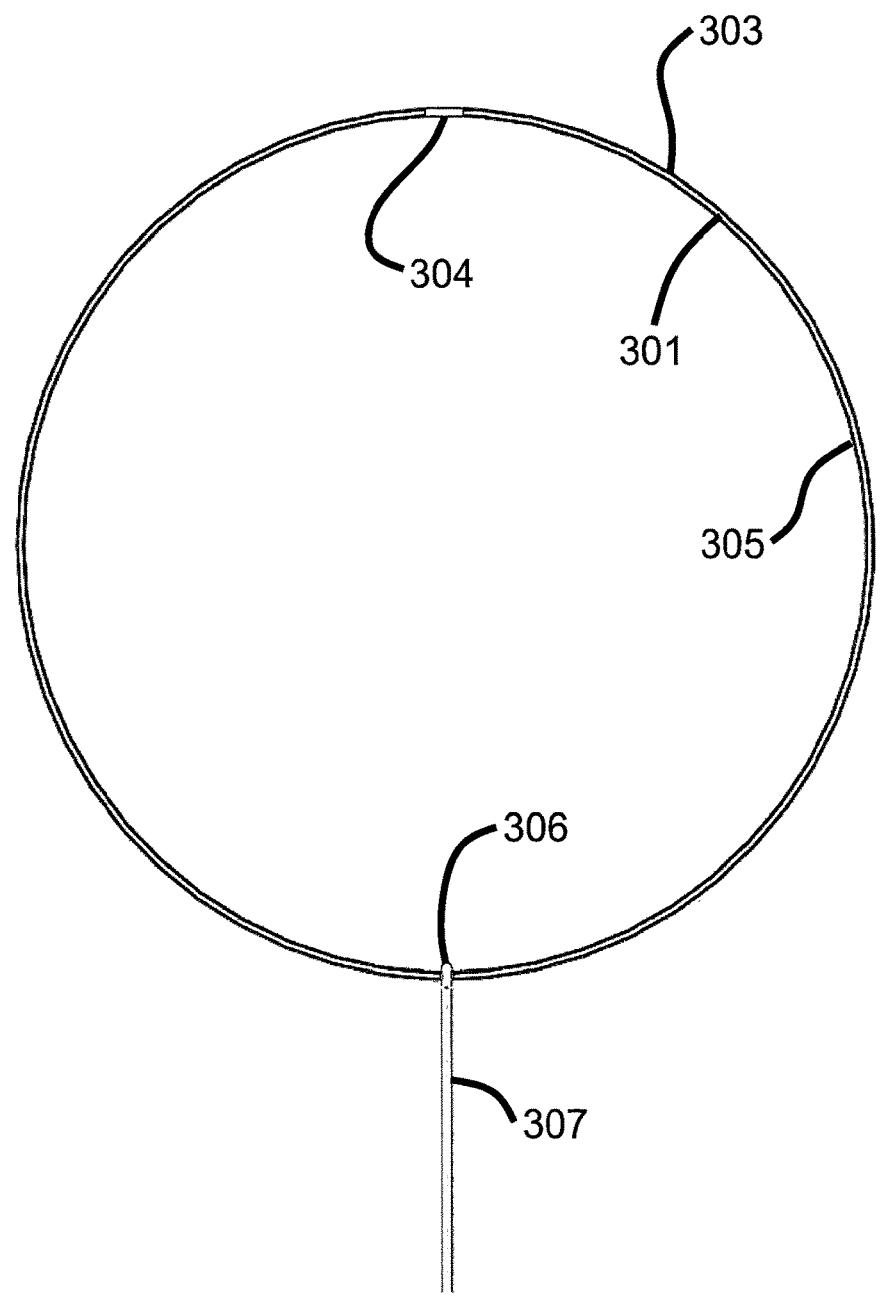

Fig. 22
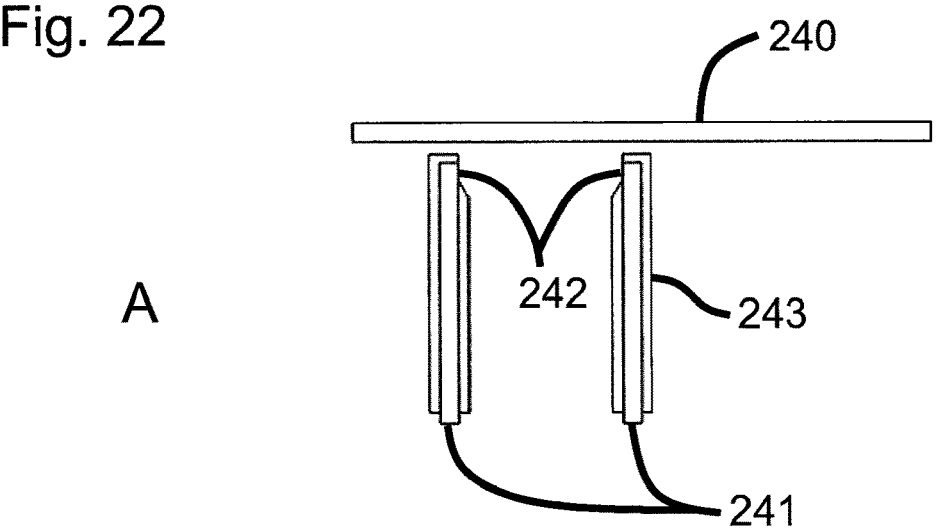
A
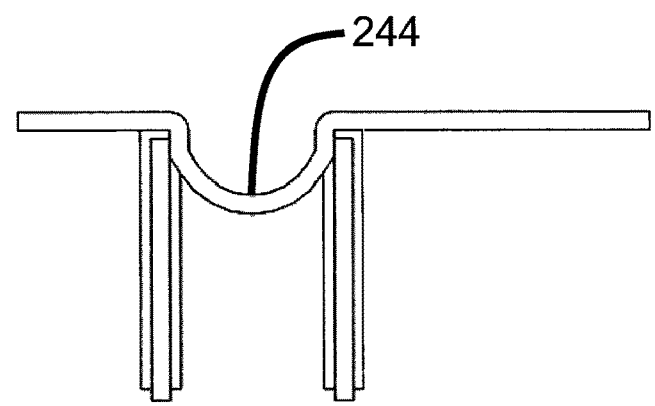
B
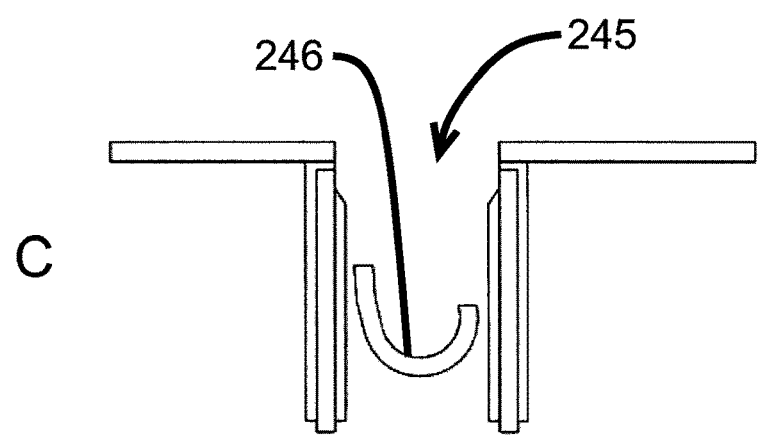
C

Fig. 22.1
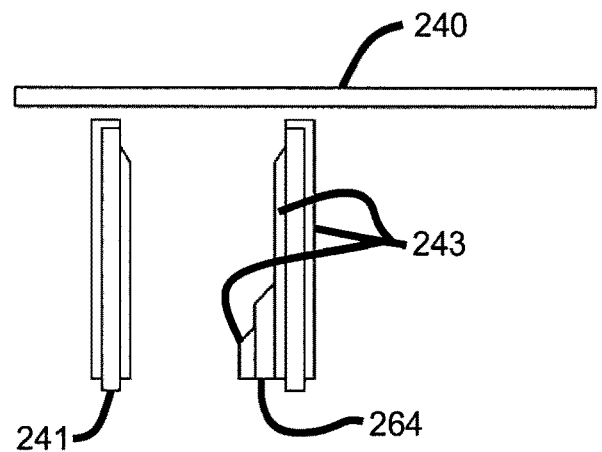
A
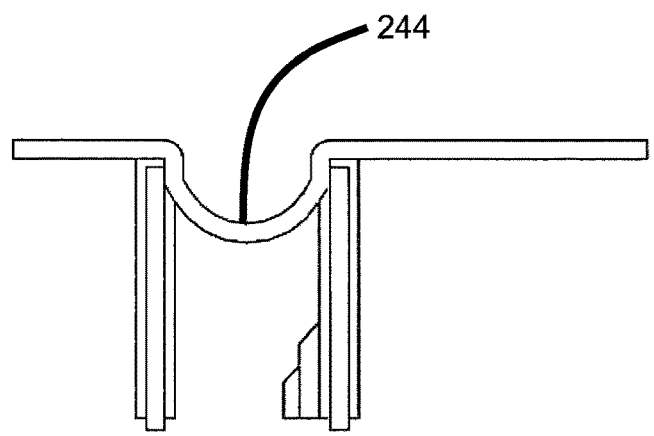
B
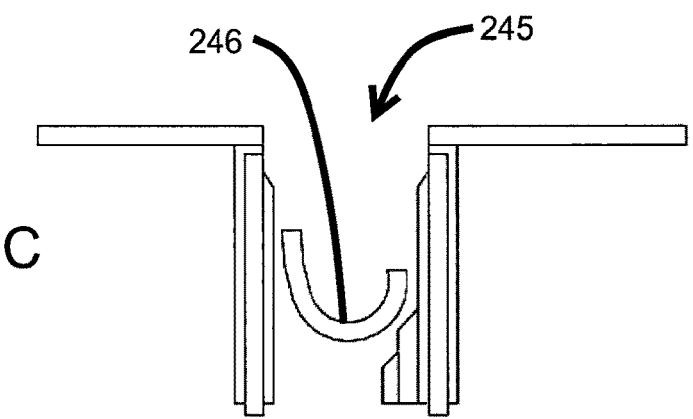
C

CAPSULOTOMY DEVICE WITH SUCTION CUP COMPRESSION CHAMBER

CROSS-REFERENCE TO RELATED APPLICATIONS

This application is the 35 USC § 371 national stage entry of PCT/US2012/049788, filed Aug. 6, 2012, which claims the benefit of U.S. Provisional Patent Application No. 61/515,358, filed Aug. 5, 2011, the disclosures of which are incorporated herein by reference.

STATEMENT REGARDING FEDERALLY SPONSORED RESEARCH

This invention was made with government support under Grant Numbers 3R44EY021023-03S1, 5R44EY021023-03, 1R43EY021023-01A1, 2R44EY021023-04, and 2R44EY021023-02, awarded by the National Institutes of Health. The government has certain rights in the invention.

BACKGROUND

This invention pertains in general to microsurgery of tissue, and more specifically to procedures and devices for accessing a tissue through another tissue layer, to cut or otherwise manipulate that tissue. For example, the procedures and devices can be used to deliver an ophthalmic surgical device through the cornea to the anterior lens capsule membrane in the anterior chamber of an eye.

Lens cataract is the leading cause of blindness worldwide and surgical treatment by cataract removal is the treatment of choice. A cataract is a clouding that develops in the lens of the eye or in its envelope. The creation of areas of opacity in the lens obstructs the passage of light. The lens of the eye is supposed to be transparent. If the lens develops opaque areas, as in a cataract, the lens must be surgically removed. If no lens is present in the eye, heavy corrective glasses are required to focus an image on the retina. The lens, however, can be replaced with an artificial intraocular lens (IOL) to provide better vision after cataract removal. There may also be other reasons such as presbyopia to replace a lens that is not serving its functions appropriately.

The removal of the lens for replacement with an IOL is a surgical procedure that requires substantial precision. The lens is completely enclosed by a membrane called the lens capsule, so the surgeon must first cut through the capsule to access the lens. It is important to cut the capsule in just the right way. If the lens capsule has been cut correctly, and not damaged during the cataract removal, then it can be used to hold an IOL. The implantation of an IOL requires the creation of an opening in the lens capsule that is precisely centered, sized, and shaped for implant stability and for optimal IOL function. The matching of the lens capsule opening size to the peripheral margins of the IOL is critical. The goal of the surgeon is to create a perfectly circular (e.g., 5.5+/−0.1 mm diameter) hole in the capsule, centered exactly on the optical axis of the eye, with no tears or defects in the edge of the hole. Tears or defects on the edge of the hole make the capsule very weak and vulnerable to losing the ability to hold the IOL properly. Different IOL designs may require a different diameter for the hole (e.g., ranging from 4.5+/−0.1 mm to 6.0+/−0.1 mm), but whatever the prescribed diameter is, the accuracy of the surgeon in actually achieving it is very important for proper outcome of the cataract surgery. This is especially true of IOLs intended to perform complex optical and focusing functions.

Creating an opening in the lens capsule with this required level of precision is a difficult task for a surgeon controlling and guiding conventional handheld cutting instruments and attempting to trace a precise circular route on the lens capsule. Currently, to perform a capsulotomy (the creation of an opening in the lens capsule), the surgeon typically manually creates a small tear in the anterior region of the lens capsule. With great caution, the surgeon then uses a small forceps to try to extend the edge of the tear so as to follow a circular path of the specified diameter and centered on the optic axis of the eye. In practice, it often happens that the hole does not end up circular, or the correct diameter, or centered on the optic axis. There can also be radial tears in the edge of the hole that greatly weaken the capsule. As a result of any of these errors, the capsule may not be able to hold the IOL properly, and optimal visual outcome cannot be achieved.

In addition to the difficulties faced by the surgeon in accessing the lens by performing a precise capsulotomy of the lens capsule, the surgeon must also be able to access the lens capsule itself. The lens is positioned in the anterior chamber of the eye. To access the lens capsule, the surgeon must create an incision in the cornea and carefully insert the capsulotomy instruments through this incision. The same requirement exists in a number of microsurgery procedures in which an incision in a first layer of tissue must be passed through before a second layer of tissue, behind or beneath that first layer, can be accessed. For the surgeon to maneuver the microsurgery instruments through the corneal incision, the incision must be of sufficient size to accommodate these instruments. However, the larger the incision, the greater the risk of infection, of corneal distortion, and of other complications. Microsurgery instruments commonly are not compact enough or are not sufficiently streamlined in shape, making it difficult for the surgeon to minimize the incision size or possibly risking tears or other damage at the incision site. Cutting elements or other sharp components are sometimes exposed during insertion, requiring the surgeon to be very precise and creating further risk of collateral damage to tissue when inserting the instrument through the incision. Further, this insertion often requires multiple steps and sometimes complex maneuvering of instruments by the surgeon, leaving little room for error. Once inserted, instruments are often not easily manipulated and the surgeon may be forced to handle and move multiple separate pieces in a small space. Any of these problems can make it very difficult for a surgeon to access a second layer of tissue behind a first layer, particularly when the second layer is tissue in a very small area, such as within the eye.

Given the drawbacks of existing treatment devices/procedures for accessing tissue, such as the lens capsule, to perform surgery, improved techniques and devices for performing microsurgery are needed.

SUMMARY

Embodiments of the invention include devices and methods for accessing a lens capsule through a cornea of an eye, for performing a capsulotomy in the eye. In one embodiment, provided herein is a method for performing a capsulotomy of a lens capsule of an eye, the method comprising: contacting the lens capsule with a cutting element; applying stress to the lens capsule along the cutting element; applying energy to the lens capsule along the cutting element during the application of stress, resulting in the cutting of a portion of the lens capsule along the cutting element. In one embodiment, the cutting element is an electrode. In another embodiment, the electrode is circular.

In one aspect, applying energy comprises applying an electric pulse to the electrode. In another aspect, applying energy comprises applying resistive heating along the cutting element. In still another aspect, the cutting element is mounted to a suction cup. In yet another aspect, the cutting element is in uniform contact with the lens capsule. In still another aspect, the stress is tensile stress.

Also provided herein in one embodiment is a method of compressing a cutting element for insertion into the anterior chamber of an eye, the method comprising: obtaining a device comprising a handpiece comprising a cutting element extended distally from the handpiece into a compression mechanism, wherein the compression mechanism comprises compression elements along the sides of the cutting element, and wherein the compression mechanism further comprises a floor and a roof, wherein the floor is proximal to the bottom of the cutting element and the roof is proximal to the top of the cutting element; and compressing the cutting element in the compression mechanism using the compression elements, wherein the floor and the roof restrict out of plane movement of the cutting element during the compression.

In one embodiment, the cutting element is mounted to a suction cup, and wherein the suction cup is compressed along with the cutting element. In another embodiment, the cutting element is an electrode. In still another embodiment, the compression elements comprise slidable arms, and wherein compressing the cutting element comprises moving the slidable arms toward each other while the cutting element is in the compression mechanism, and retracting the cutting element into a tip of the handpiece of the device. In yet another embodiment, the compression elements comprise fixed walls tapered to a hole for removal of the cutting element, and wherein compressing the cutting element comprises retracting the cutting element from the compression mechanism into a tip of the handpiece of the device. In one aspect, the compression mechanism is attached to the device. In another aspect, the tip of the device is inserted into the compression mechanism.

In one embodiment, disclosed herein is a method of inserting a cutting element into the anterior chamber of an eye, the method comprising: obtaining a compressed cutting element mounted within a handpiece of a device; moving a tip of the device through an incision in a cornea of the eye; deploying the compressed cutting element out through the tip of the handpiece into the anterior chamber of the eye. In another embodiment, the cutting element is mounted to a sliding element within the handpiece, wherein deploying the compressed cutting element comprises moving the sliding element distally along the handpiece. In still another embodiment, the cutting element is mounted to a suction cup.

Also provide herein, in one aspect, is a method for performing a capsulotomy of a lens capsule of an eye, the method comprising: obtaining a compressed cutting element mounted within a handpiece of the capsulotomy device; moving a tip of the capsulotomy device through an incision in a cornea of the eye; deploying the compressed cutting element out through the tip of the handpiece into an anterior chamber of the eye; expanding the cutting element inside the anterior chamber of the eye into a cutting position on the lens capsule; cutting a portion of the lens capsule using the cutting element; and removing the capsulotomy device from the eye.

In one embodiment, obtaining a compressed cutting element comprises: obtaining a cutting element extended distally from the handpiece of the capsulotomy device, wherein the cutting element is situated in a compression mechanism, wherein the compression mechanism comprises compression elements along the sides of the cutting element, wherein the compression mechanism further comprises a floor and a roof, and wherein the floor is proximal to the bottom of the cutting element and the roof is proximal to the top of the cutting element; and compressing the cutting element in the compression mechanism using the compression elements, wherein the floor and the roof restrict out of plane movement of the cutting element during the compression. In a further embodiment, the compression elements comprise slidable arms, and wherein compressing the cutting element comprises moving the slidable arms toward each other while the cutting element is in the compression mechanism, and retracting the cutting element into a tip of the device. In another further embodiment, the compression elements comprise fixed walls tapered to a hole for removal of the cutting element, and wherein compressing the cutting element comprises retracting the cutting element from the compression mechanism into a tip of the device. In one aspect, the compression mechanism is attached to the capsulotomy device. In another aspect, the tip of the capsulotomy device is inserted into the compression mechanism.

In one embodiment, the cutting element inside the anterior chamber of the eye into a cutting position on the lens capsule comprises applying stress to the lens capsule along the cutting element. In another embodiment, the stress is tensile stress. In still another embodiment, the cutting element is in uniform contact with said lens capsule before the cutting. In yet another embodiment, the cutting element is mounted to a sliding element within the handpiece, wherein deploying the compressed cutting element comprises moving the sliding element distally along the handpiece. In still another embodiment, the cutting element is mounted to a sliding element within the handpiece and wherein deploying the compressed cutting element further comprises translating the sliding element distally to move the cutting element within the handpiece, out through the tip and to the lens capsule within the anterior chamber, the cutting element expanding once it passes out of the tip of the handpiece.

In one aspect, deploying the compressed cutting element further comprises: translating the cutting element within the handpiece and out through the tip of the handpiece into the anterior chamber; and permitting the cutting element to expand back to its prior shape within the anterior chamber. In another aspect, cutting a portion of the lens capsule further comprises: applying suction to the suction cup, the suction securing a flared skirt of the suction cup against the lens capsule and pulling tissue against the cutting element; and cutting the tissue of the lens capsule pulled against the cutting element.

In one embodiment, the cutting element is an electrode. In another embodiment, cutting out the portion of the tissue further comprises applying electrical current to the electrode via electrical leads that allow current to travel in two directions around a continuous element of the electrode that uniformly heats the portion of the tissue to sever the tissue. In still another embodiment, the electrode is circular. In yet another embodiment, the cutting element comprises two concentric electrodes configured adjacent to each other. In another embodiment, the cutting element comprises two electrodes separated to induce current flow through the lens capsule.

In one aspect, the cutting element is mounted to a suction cup. In another aspect, the method comprises applying a suction to the suction cup for securing the suction cup to the lens capsule of the eye after expanding the cutting element inside the anterior chamber of the eye into a cutting position on the lens capsule, the suction pulling tissue of the lens capsule against the cutting element. In still another aspect, the application of suction to the suction cup causes the lens capsule to be pulled against the cutting element causing uniform circular contact between the lens capsule and the cutting element.

In one embodiment, the suction cup further comprises a lens capsule removal element on the underside of the suction cup within an area bounded by the cutting element for attaching a portion of the lens capsule that has been completely severed from the rest of the lens capsule. In a further embodiment, the lens capsule removal element is selected from the group consisting of: a second suction cup; a barb; and a hook. In another embodiment, removing the capsulotomy device comprises reducing the suction applied to the suction cup for releasing the suction cup from tissue of the lens capsule. In yet another embodiment, the method comprises withdrawing the suction cup with the portion of the excised lens capsule through the incision.

In one aspect, the cutting element is mounted to a sliding element within the handpiece and wherein removing the capsulotomy device further comprises: translating the sliding element proximally to move the cutting element away from the lens capsule within the anterior chamber, through the tip, and into the handpiece; and withdrawing the tip of the capsulotomy device through the incision in the cornea and away from the eye.

Also provided herein, in some embodiments, is a capsulotomy device for accessing a lens capsule through a cornea of an eye, the device comprising: a handpiece having a tip that is insertable into an incision in a cornea of an eye; a sliding element slidably disposed for translation within the handpiece; a cutting element mounted to the sliding element and moveable into and out of the handpiece using the sliding element, the cutting element compressed in the handpiece and configured to expand inside an anterior chamber of an eye into a cutting position on a lens capsule.

In one embodiment, the capsulotomy device comprises a compression mechanism associated with the cutting element and the handpiece to compress the cutting element for insertion into the tip of the handpiece. In a further embodiment, the compression mechanism comprises compression elements along the sides of the cutting element, and wherein the compression mechanism further comprises a floor and a roof, wherein the floor is proximal to the bottom of the cutting element and the roof is proximal to the top of the cutting element when placed in the compression mechanism. In another further embodiment, the compression elements comprise slidable arms. In still another further embodiment, the compression elements comprise fixed walls tapered to a hole for removal of the cutting element from the compression mechanism into a tip of the handpiece of the device.

In one aspect, the cutting element is an electrode, and the capsulotomy device comprises one or more electrical elements for delivering current to an electrical lead connected to the electrode to heat the electrode for excising a portion of tissue of the lens capsule. In a further aspect, the electrode is circular. In another aspect, the electrode comprises a continuous element along which current can travel in two opposite directions for conducting current uniformly around the portion of the tissue to be severed. In still another aspect, the electrode comprises an upper ring that connects to the electrical lead and a lower ring that connects to the upper ring at two locations on opposite sides of the lower ring, and wherein current travels from the upper ring to the lower ring via one of the locations and then travels around both sides of the lower ring to the location on an opposite of the lower ring to evenly distribute the current around the lower ring that is in contact with the lens capsule. In yet another aspect, the cutting element comprises two concentric adjacent electrodes, and further comprising one or more electrical elements for delivering current to an electrical lead connected to the electrodes to conduct current along tissue between the two adjacent electrodes. In still another aspect, the cutting element comprises two electrodes, and further comprising one or more electrical elements for delivering current to an electrical lead connected to the electrodes to conduct current along tissue between the two adjacent electrodes.

In one embodiment, the cutting element is mounted to a suction cup. In a further embodiment, the device comprises one or more suction elements connected to the suction cup for applying suction to the suction cup. In one embodiment, the suction cup further comprises a flared skirt extending from an edge of the suction cup for securing the suction cup against the lens capsule to form a vacuum seal. In still another embodiment, the suction cup comprises a lens capsule removal element on the underside of the suction cup within a barrier formed by the cutting element. In a further embodiment, the lens capsule removal element is selected from the group consisting of: a second suction cup, a barb, and a hook.

In one aspect, the device comprises a piston connected to an end of the sliding element opposite the cutting element and slidably associated with the handpiece for, responsive to an outside force, translating the sliding element distally to move the cutting element within the handpiece, out through the tip and to the lens capsule within the anterior chamber. In another aspect, a knob connected via a slot in a housing of the handpiece to a side of the sliding element for, responsive to an outside force, translating the sliding element distally to move the cutting element within the handpiece, out through the tip for positioning against the lens capsule within the anterior chamber. In still another aspect, the tip at a distal end of the handpiece comprises an opening for containing the compressed cutting element as it is translated into the tip for insertion of the tip into the incision.

In one embodiment, provided herein is a method for accessing a second layer of tissue behind a first layer of tissue for performing microsurgery or therapeutic work, the method comprising: obtaining a foldable structure of a microsurgery device compressed for deployment through a tip of the capsulotomy device, the foldable structure mounted to a sliding element disposed within the handpiece therein; moving a tip of a microsurgery device through an incision in the first layer of tissue, the microsurgery device comprising a handpiece; translating the sliding element distally within the handpiece to deploy the compressed foldable structure out of the tip of the handpiece past the first layer of tissue, the foldable structure expanding into an operational position on the second layer of tissue; and engaging in microsurgery or therapeutic work on a portion of the second layer of tissue.

In one aspect, obtaining a compressed foldable structure comprises applying pressure to a foldable structure of a microsurgery device to compress the foldable structure. Om another aspect, engaging in microsurgery or therapeutic work further comprises cutting a portion of the second layer of tissue with a cutting element mounted to the foldable structure.

Also provide herein, in one embodiment, is a device for accessing a second layer of tissue behind a first layer of tissue for performing microsurgery or therapeutic work, the device comprising: a handpiece having a tip for insertion through an incision in the first layer of tissue; a sliding element slidably disposed for translation within the handpiece; a foldable structure mounted to the sliding element for movement into and out of the handpiece; an operational element associated with the foldable structure for engaging in microsurgery or therapeutic work on the second layer of tissue.

In one aspect, the device comprises a compression mechanism associated with the foldable structure and the handpiece to allow compression of the foldable structure. In a further embodiment, the compression mechanism comprises compression arms positioned adjacent to the foldable structure. In another further embodiment, the compression mechanism comprises compression elements along the sides of the foldable structure, and wherein the compression mechanism further comprises a floor and a roof, wherein the floor is proximal to the bottom of the foldable structure and the roof is proximal to the top of the foldable structure when placed in the compression mechanism. In still another embodiment, the compression elements comprise slidable arms. In yet another embodiment, the compression elements comprise fixed walls tapered to a hole for removal of the foldable structure from the compression mechanism.

In one aspect, the operational element further comprises a cutting element mounted to the foldable structure for cutting a portion of the second layer of tissue. In another aspect, the cutting element is an electrode.

In one embodiment, provided herein is a device for performing microsurgery on a layer of tissue, the device comprising: a handpiece having a tip comprising a cutting element; a sliding element slidably disposed for translation of the cutting element within the handpiece; a foldable structure mounted to the sliding element for movement into and out of the handpiece; an operational element associated with the foldable structure for engaging in microsurgery or therapeutic work on the layer of tissue. In one embodiment, the cutting element is an electrode. In another embodiment, the electrode is linear. In still another embodiment, the electrode is curved. In yet another embodiment, the electrode is non-circular.

BRIEF DESCRIPTION OF THE DRAWINGS

FIG. 2A-E shows the conceptual sequence of steps for compression of the suction cup to fit inside the inserter for entry into the eye, according to an embodiment of the invention.

FIG. 3A-D is a top perspective view of a low friction compression device with converging sidewalls, according to an embodiment of the invention.

FIG. 7A1 is a partial side view cross section of the suction cup within a compression chamber, according to an embodiment of the invention. FIG. 7A2 is a partial top view of the suction cup in the compression chamber in an open position, according to an embodiment of the invention. FIG. 7A3 is a partial top view of the compression chamber in a closed position, according to one embodiment of the invention.

FIG. 11A2 depicts a side elevation view of an electrode design and current flow, according to an embodiment of the invention. FIG. 11A3 is a view from below an electrode cutting device. FIG. 11A4 is an overhead view of an electrode cutting device.

FIGS. 22A-C depict steps for cutting a membrane or tissue with a cutting element comprising an electrode, according to an embodiment of the invention. FIGS. 22.1A-C depict steps for cutting a membrane or tissue with a cutting element comprising two electrodes, according to an embodiment of the invention.

Figure 1:
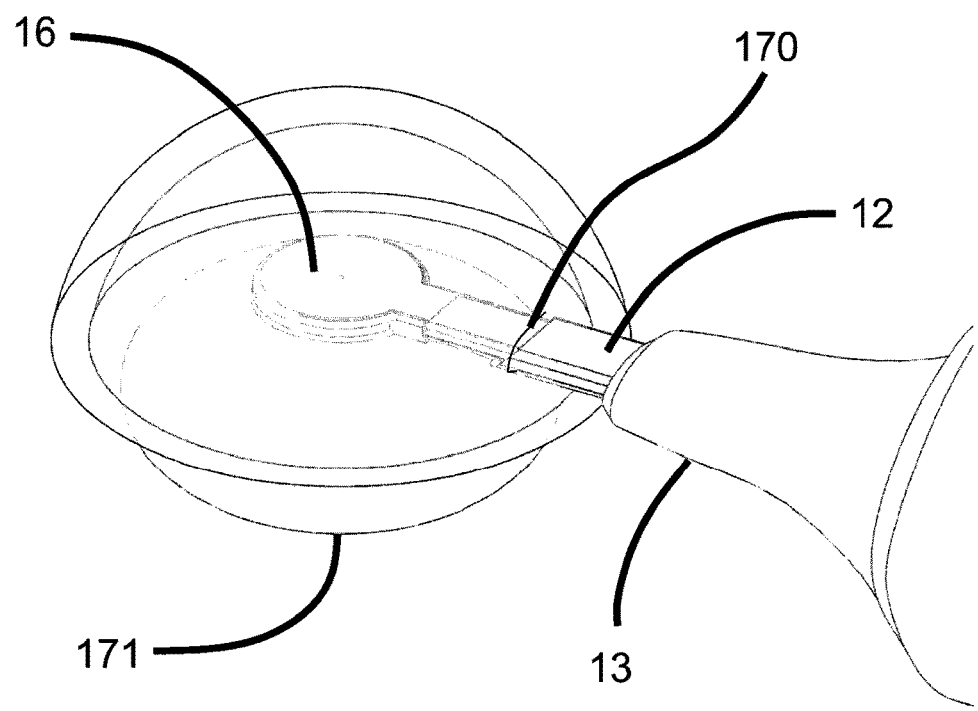
FIG. 1 is a top perspective view of the microsurgery/capsulotomy device with a suction cup deployed and in contact with the lens capsule of the eye, according to an embodiment of the invention.

The figures depict an embodiment of the present invention for purposes of illustration only. One skilled in the art will readily recognize from the following description that alternative embodiments of the structures and methods illustrated herein may be employed without departing from the principles of the invention described herein.

DETAILED DESCRIPTION

Microsurgery/Capsulotomy Device

Embodiments of the invention are described herein in the context of a lens capsule surgery in which a portion of the anterior surface of a lens capsule is cut. This technique may be used for performing treatment for cataracts in which all or a portion of a lens located within the lens capsule is removed from the eye. The procedure may also be used to create an access hole in the lens capsule through which to implant an artificial lens (e.g., an intraocular lens, or IOL) within the lens capsule. Though often described herein in terms of performing lens capsule surgery, the devices and procedures are not limited to lens capsule surgery, but can also be useful in other treatments of the eye, such as a corneal surgery, treatments for glaucoma, microfenestration of the optic nerve, surgeries involving decemet's membrane, among others. Furthermore, the devices and procedures may also be useful in the delivery of pharmacologic, biologic, and chemical entities and therapeutics. The devices and procedures can also be used to deliver fluids in addition to suction, and the delivery can be specifically localized (e.g., by the suction cup) limiting exposure only to desired tissues. In addition, the devices and procedures may be useful for industrial applications or performing other medical procedures outside of the eye, such as procedures involving excision of delicate membranes or tissue structures, fenestration of brain dura, vascular tissues and others. The devices and procedures can also be used outside of the body, on tissue excised and separate from the body, for industrial applications, etc. In these other types of applications, the procedures and devices function generally in the same manner as described regarding the lens capsule surgery, though the components may be differently arranged, sized, shaped to accommodate different tissue.

In one embodiment, the device uses suction force to stretch a capsular membrane over the thin edge of a circular metal electrode, thereby establishing a state of uniform, circular contact between the electrode and the lens capsule, to increase tensile stress within the membrane exactly where cutting is desired, e.g., a circle on the capsular membrane. Then a short burst of electrical energy is passed through the electrode. This causes more stress at the prestressed line of cutting and completes the cut there. The duration of the electrical pulse is less than 10 millisecond (preferably about 10 to 100 microseconds or less) so that only a small volume of tissue is heated by it. The nature of the pulse may be DC, or AC (radio waves e.g., 1 MHz, or microwaves e.g., 2.4 GHz).

In another embodiment, a circular metal electrode, without suction cup, is carefully placed into uniform circular contact with the lens capsule to effect cutting in the same manner.

The term "pulse" as used herein refers to the length of time the electrical pulse is on, for example 100 microseconds. If the pulse is a DC pulse the current is going in only one direction (but amplitude may be changing) during the entire 100 microseconds. If it is an AC pulse the current reverses direction during the 100 microseconds. If the AC frequency is in the RF or in the microwave range there will be many cycles during the 100 microsecond pulse. The frequency and amplitude may change or slow during the 100 microseconds and that kind of pulse is called a "chirp"), and the current path may go around the ring of metal, or may go from the ring through tissue to a return electrode.

FIG. 1 is a top perspective view of the microsurgery/capsulotomy device with the suction cup deployed/foldable structure 16 deployed. The inserter 12 (a thin walled rigid tube) is inserted through an incision in the cornea 170 of an eye. The suction cup 16 is then extended through the inserter, and centered over the optic axis of the lens 171 or another desired position. Suction is applied to force the suction cup and the circular electrode therein, against the surface of the capsular membrane where the cut is to be made.

A problem solved by this invention is how to compress the suction cup or electrode so it can fit inside the inserter for entry into the eye. This is particularly useful in instances where the suction cup and any embedded or associated components such as electrodes are fragile or easily plastically deformed. It is also useful in instances where only electrodes are compressed without a suction cup. FIGS. 2A-2E show the conceptual sequence of steps in one embodiment. FIG. 2A shows a schematic top view of the initial configuration as shipped. A suction cup 100 is located between compressor arms 101. The suction cup is extended out from the inserter 102 whose vertical walls are seen here in cross section. The suction cup is attached to a stem 103 that has a lumen for fluidic transport. In this embodiment, the suction cup is packaged this way so it is not subject to any applied stress prior to use. In FIG. 2B the compression arms have been pushed towards the center so that the width of the suction cup is less than or equal to the width of the lumen of the inserter. The height of the suction cup (during compression) is constrained by the roof and floor of the compression chamber to be less than or equal to the height of the lumen of the inserter. Thus, during compression, the suction cup and any associated parts enclosed within or attached to the suction cup are prevented from folding, or twisting out of plane. By compressing the suction cup prior to pulling it into the inserter, the force needed to pull it in is reduced. In one embodiment, prior to compressing the suction cup, the user injects a lubricant, e.g., saline or viscoelastic (viscoelastic substance used in cataract surgery), into the compression chamber to reduce friction forces.

For the compression of electrodes alone, the electrode is constrained by the roof and floor of the compression chamber with the suitable height to prevent out of plane deflections.

FIG. 2C schematically shows the configuration after the compressed suction cup has been pulled into the inserter. In FIG. 2D the compression chamber has been taken away, and the end of the inserter is exposed so it can be inserted through the corneal incision. FIG. 2E shows the suction cup as it would be extended out of the inserter and deployed within the anterior chamber of the eye. In one embodiment, the compression may be performed manually by pushing on the compression arms. In another embodiment, the compression arms may be moved using a form of actuation.

This in-plane compression is also beneficial for compressing a suction cup containing a fragile insert such as an electrode, or for the compression of an electrode or electrodes without a suction cup. In one aspect, the invention minimizes stresses and twisting of fragile elements.

FIGS. 3A-3D show another low friction compression device. In this case, converging sidewalls 160 gradually compress the suction cup 100 as it is pulled into the inserter 102. In one embodiment, friction is low because the compression chamber is flooded with saline, or viscoelastic, or other lubricants, prior to use. The floor and roof of the compression chamber physically constrain the suction cup or electrode, and prevent the suction cup or electrode from deflecting out of plane. Without the shaped converging sidewalls, all of the work of compression would have to occur at the entrance to the inserter and the required force would be greater. In FIG. 3B the suction cup is fully inside the inserter. In FIG. 3C the compression chamber has been removed. FIG. 3D shows the device as it would appear after the inserter has been pushed through the corneal incision and the suction cup deployed within the anterior chamber (see also FIG. 7A1 and FIG. 10B). In one embodiment, the low friction compression device is used for a suction cup containing an electrode or with electrodes alone.

Figure 4:
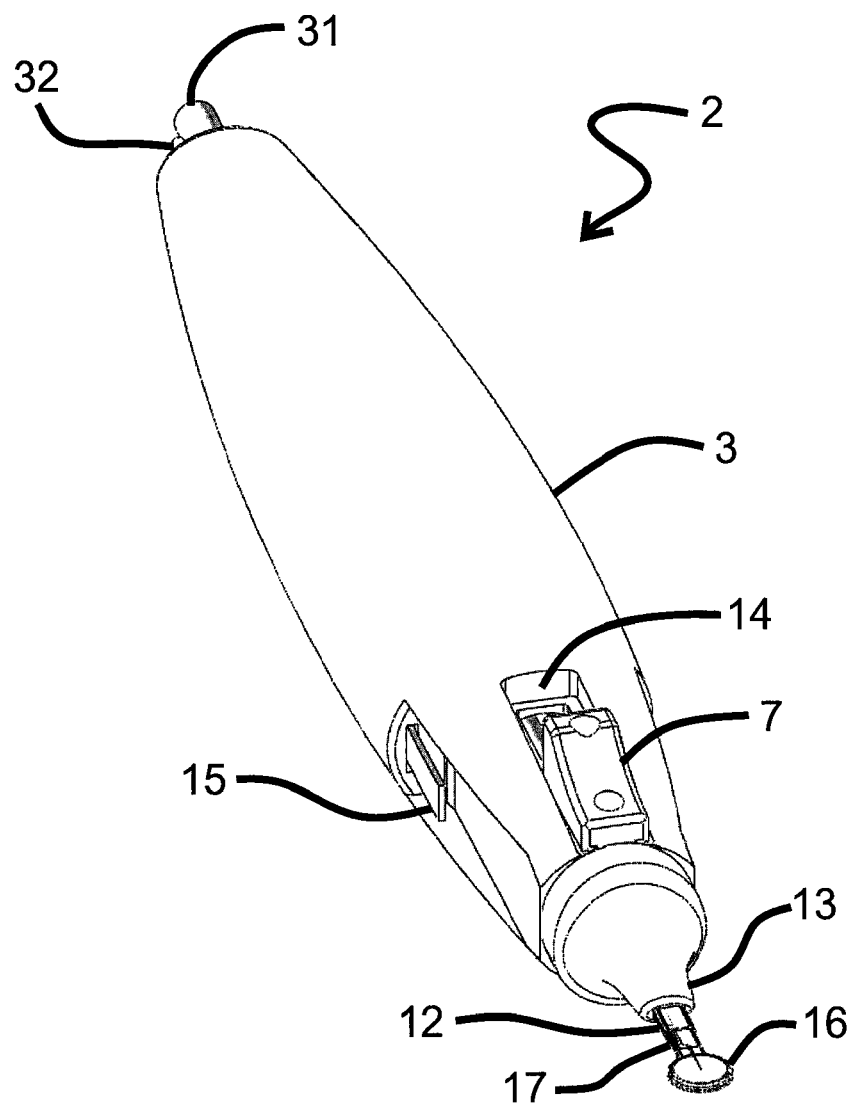
FIG. 4 is a top perspective view of the microsurgery/capsulotomy device with the suction cup deployed, according to an embodiment of the invention.
Figure 5:
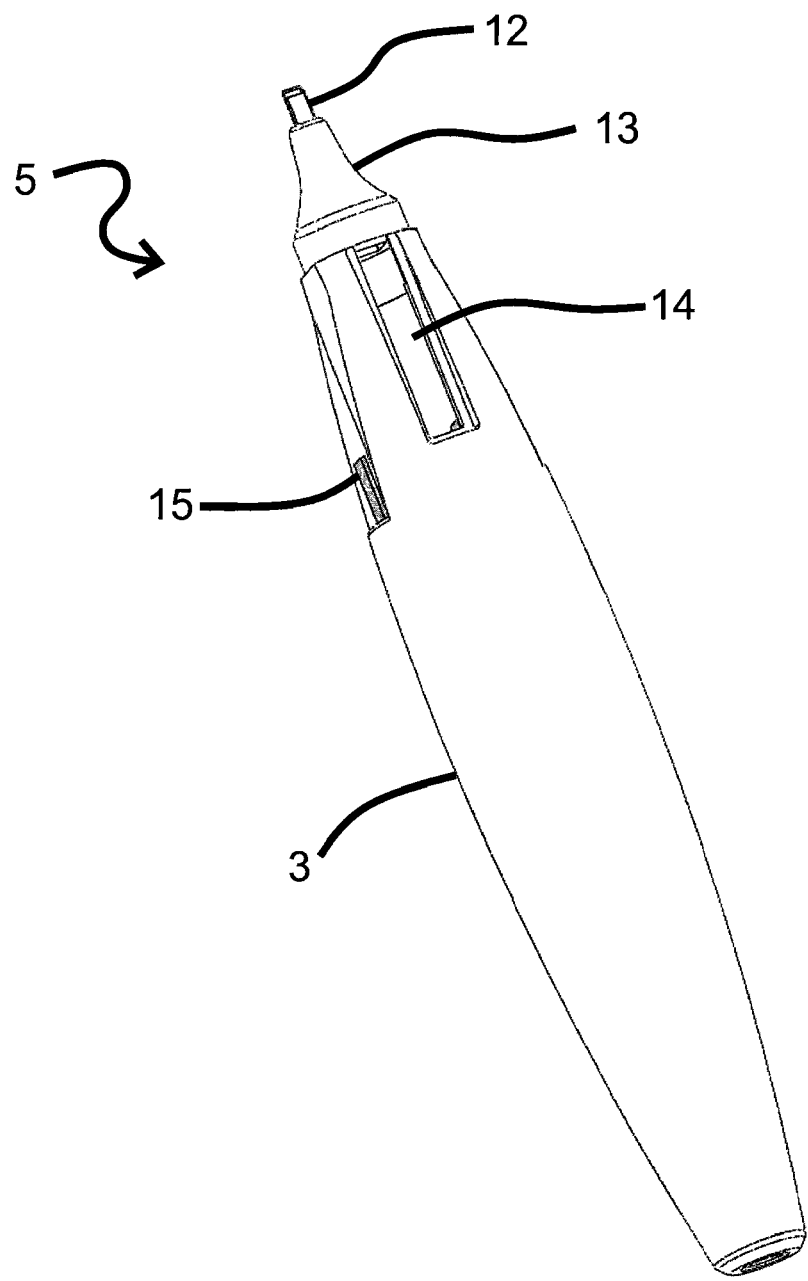
FIG. 5 is a top perspective view of the nonsliding unit of the microsurgery/capsulotomy device, according to an embodiment of the invention.

FIG. 4 depicts a top perspective view of the microsurgery/capsulotomy device with the suction cup deployed, according to an embodiment of the invention. It shows an overview of the hand piece 2 with the suction cup 16 deployed, and without the compression chamber present. The hand piece is comprised of two assemblies: a sliding unit 4 (shown in FIG. 6), and a nonsliding unit 5 (shown in FIG. 5). The nonsliding unit has a body 3 that is held in the hand of the user and provides the mechanical foundation to support the other components. It has a nosepiece 13 that is attached to the body. The inserter 12 is attached or glued to the distal end of the nosepiece. In another embodiment, the body 3, nosepiece 13, and the inserter 12 may be formed as one part. The distal end of the inserter is tapered to facilitate its entry through the corneal incision that is made by the surgeon.

Figure 6:
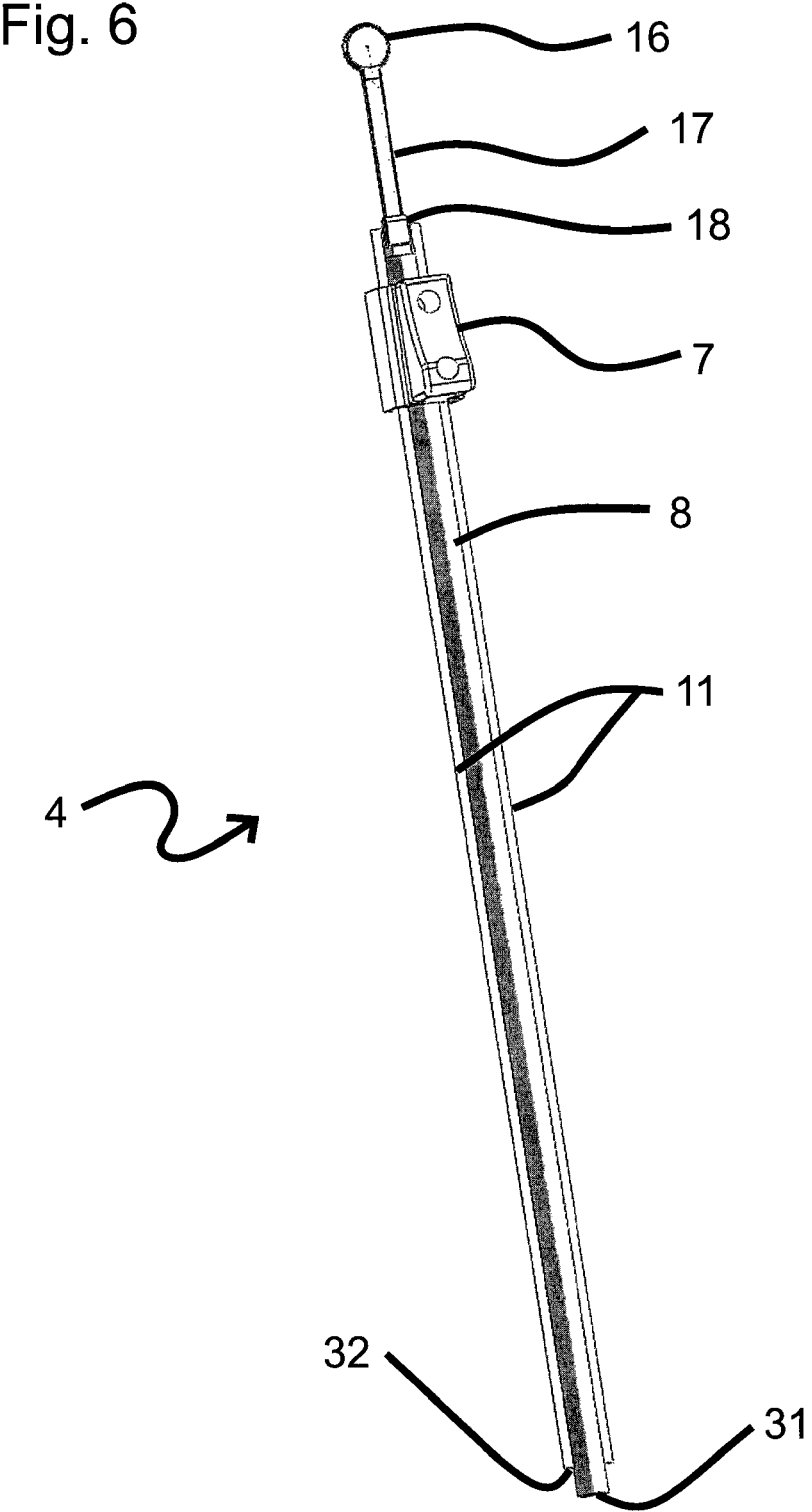
FIG. 6 is a top perspective view of the sliding unit of the microsurgery/capsulotomy device attached to the suction cup, according to an embodiment of the invention.

The sliding unit depicted in FIG. 6 includes the suction cup 16, which is a deformable elastomer (e.g., polyurethane or silicone, Shore A durometer of about 80). The suction cup is attached to a stem 17 which has at least one lumen for fluidic or gas transport, and may comprise at least one electrical conductor. The stem is attached to a suction tube 8 by means of a fitting 18. The suction tube has at least one lumen for fluidic or gas transport. The other end of the suction tube has a connector 31 for connection to a vacuum source or fluid supply. There can be one or more electrical conductors 32 to connect the stem to an external electrical potential by means of an electrical connector 32. A thumbslide 7 fits within the guide slot 14 of the body 3 (FIG. 5) to allow axial translation (without rotation) of the sliding unit relative to the nonsliding unit, from a predetermined starting point to a predetermined ending point.

Figure 7:
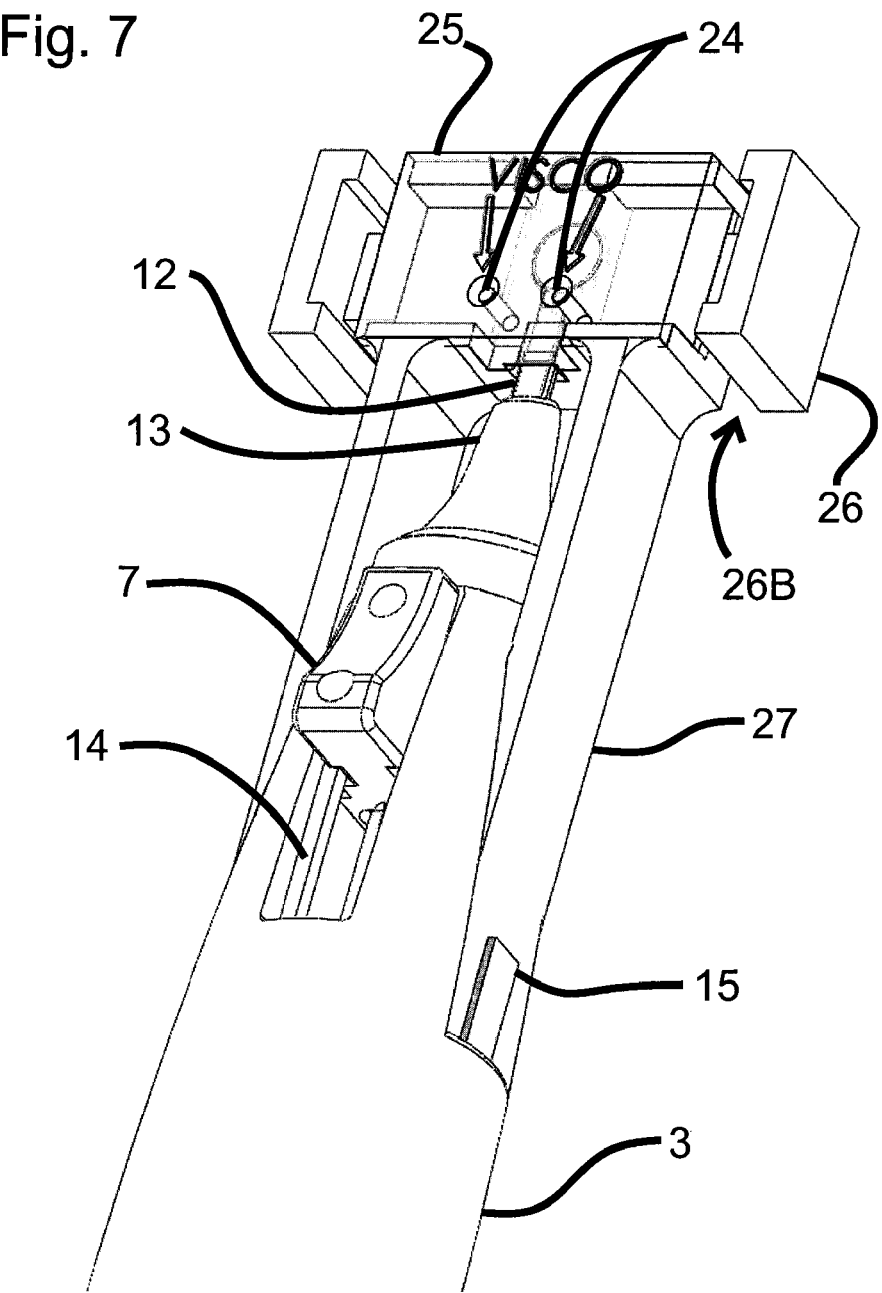
FIG. 7 is a top view of the handpiece with a compression chamber attached to it, according to an embodiment of the invention.
Figure 9:
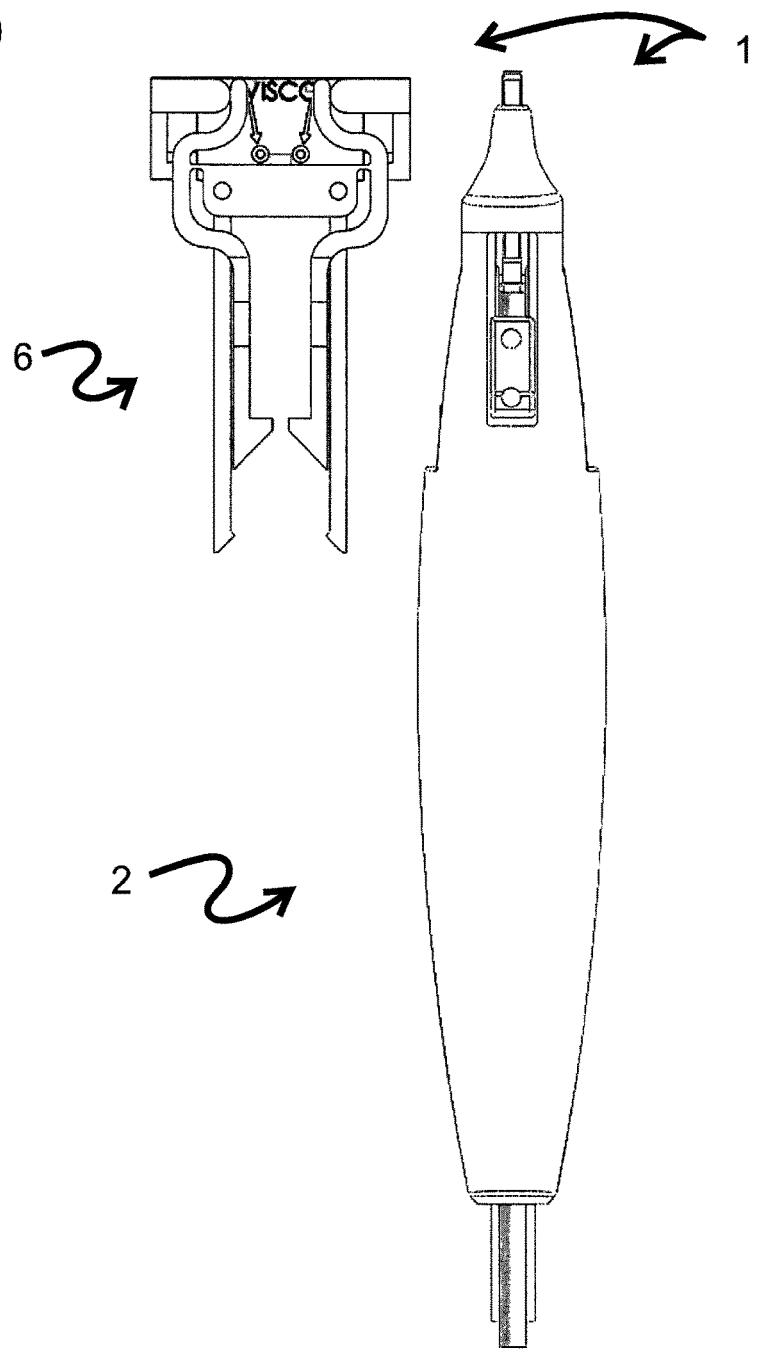
FIG. 9 is a top view of a compression chamber and a microsurgery/capsulotomy device, according to an embodiment of the invention.
Figure 9B:
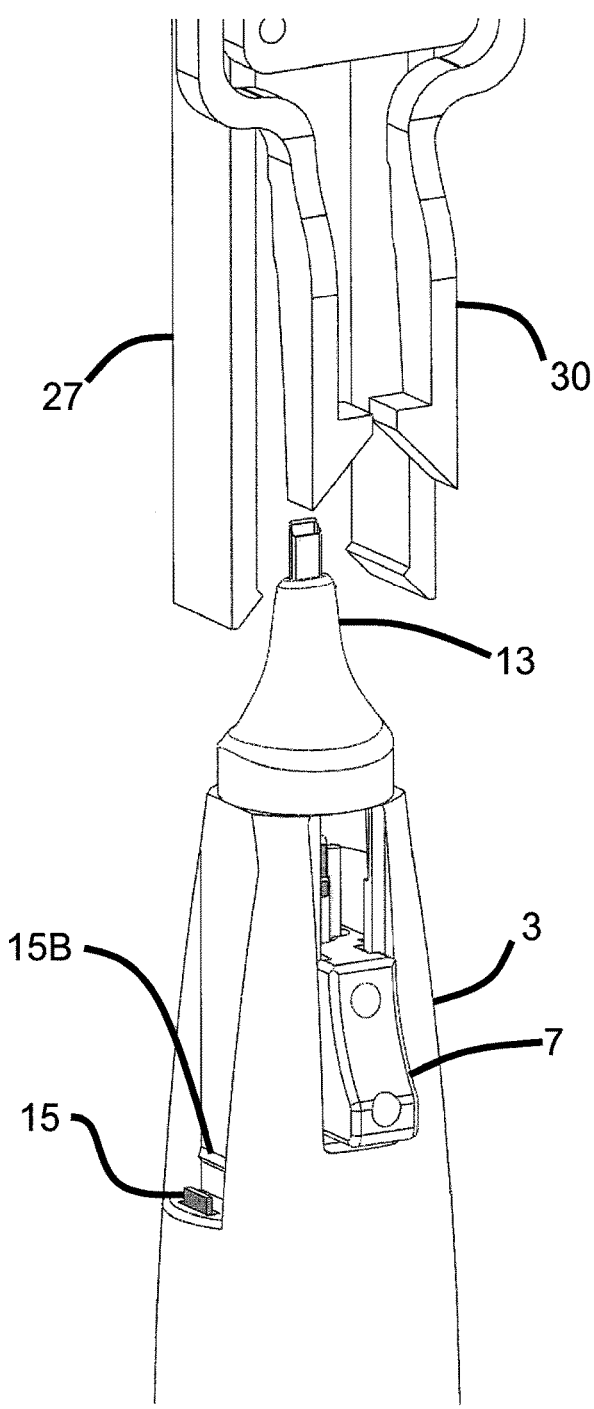
FIG. 9B is a partially exploded top perspective view of the site of attachment of the compression chamber that is removably attached to the microsurgery/capsulotomy device, according to an embodiment of the invention.

FIG. 7 shows an embodiment of the handpiece with a compression chamber attached to it. The first step in use is to lubricate the compression chamber containing the suction cup and/or electrodes. This can be accomplished by injecting viscoelastic or a suitable lubricant through one or more ports 24 to fill the space around the suction cup. Then the two compression arms 26 are pushed towards the centerline to compress the suction cup so that it will fit inside the inserter 12. Over compression is prevented by stops in the chamber structure such as when gap 26B is closed (i.e. side member 26 contacts the chamber base and can't go any further). The roof and floor of the compression chamber are flat and parallel to each other, creating a space just large enough to accommodate the suction cup and any components. This prevents the suction cup from deflecting out of plane. In one embodiment, the device is packaged and shipped in the configuration as shown in FIG. 7 with the suction cup located in the compression chamber, but not compressed. After the suction cup is lubricated, compressed, and pulled into the inserter, then the compression chamber can be removed from the handpiece. For the compression chamber to be removed, latching beams 27 must deflect away from the centerline to slide over detents 15B (see FIG. 9B) on the body of the handpiece. This deflection will be prevented by the presence of chamber latch locks 15. Chamber latch locks slide back out of the way when the thumbslide 7 is slid back to pull the suction cup into the inserter to prevent out-of-sequence operation.

Figure 2:
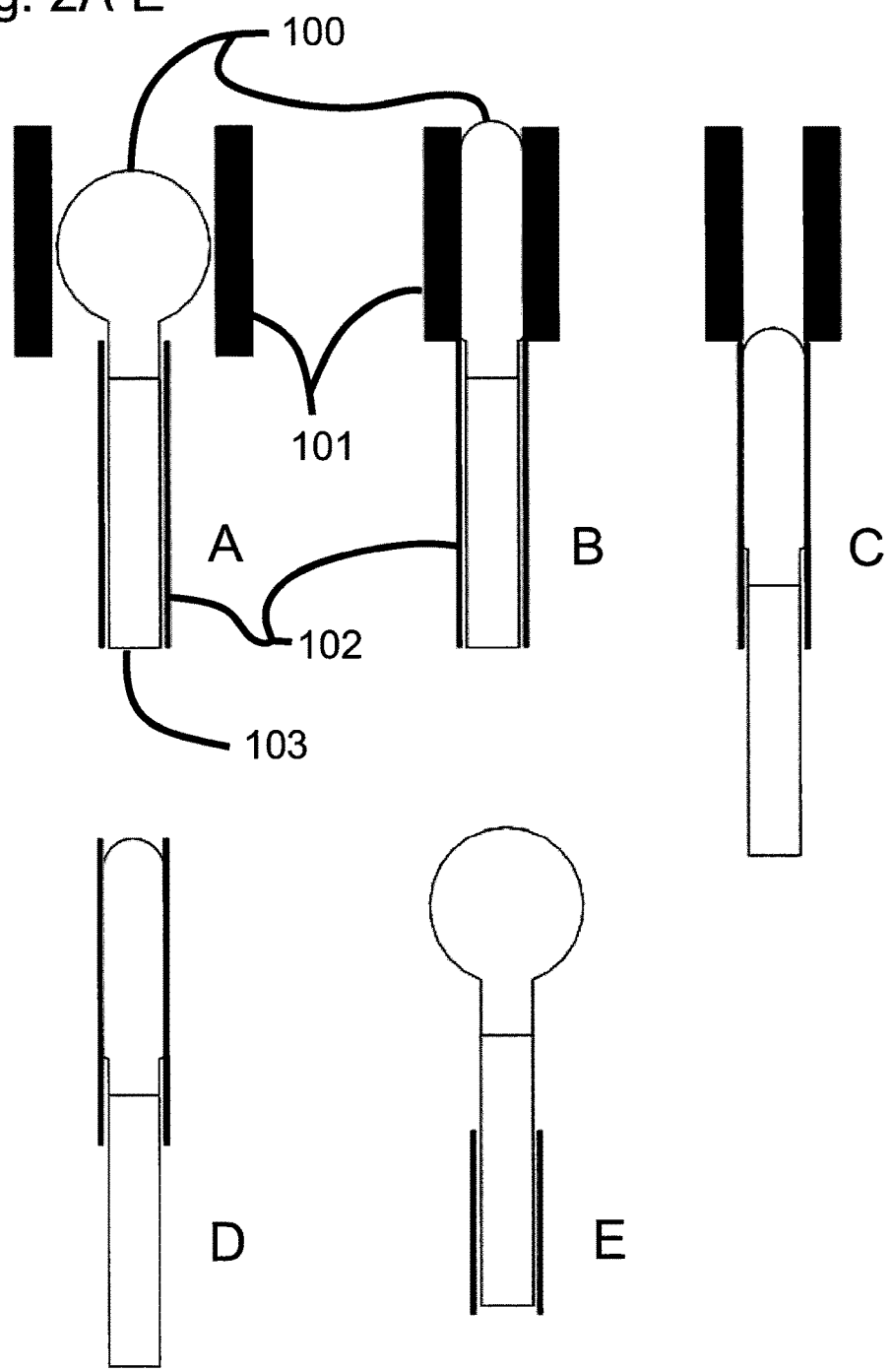
Figure 3:
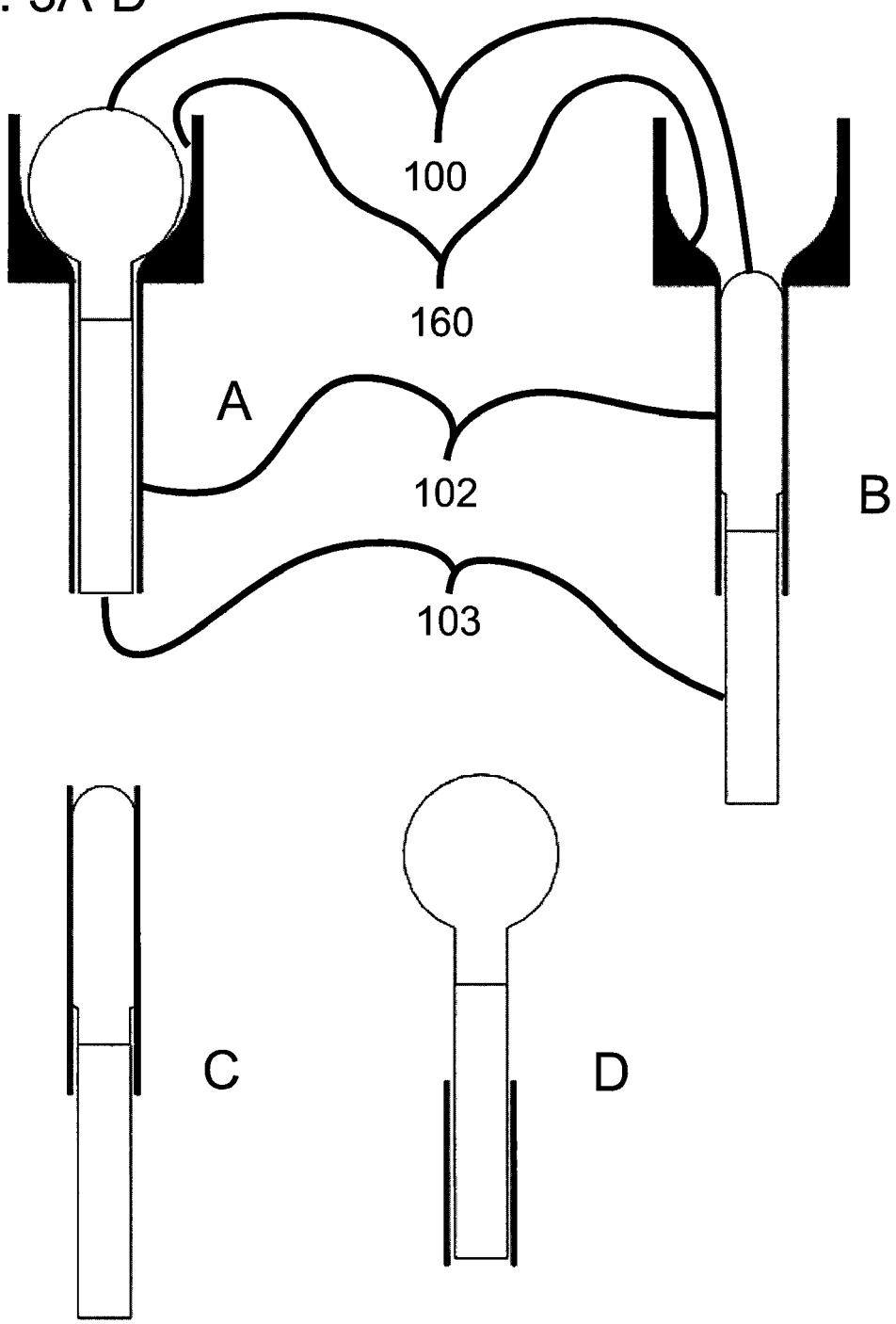
Figure 7B:
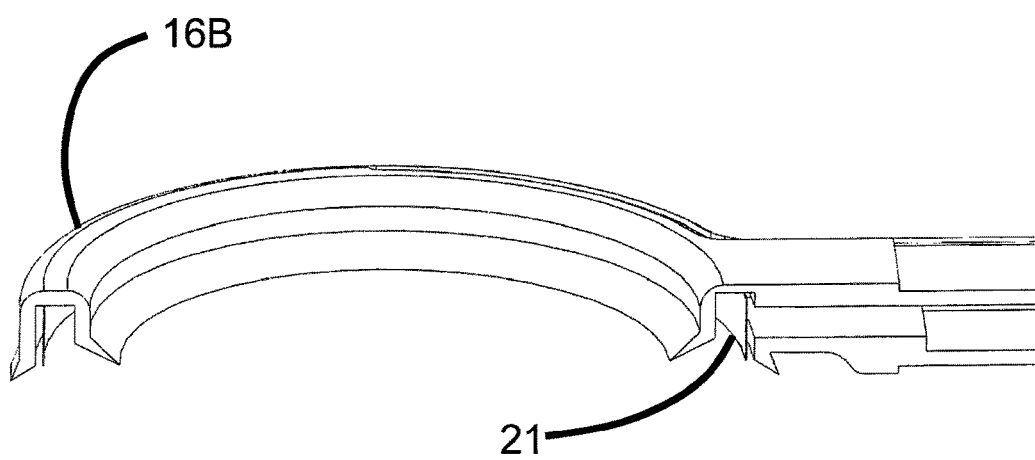
FIG. 7B is a partial cross-sectional view of the suction cup, according to one embodiment of the invention.
Figure 8:
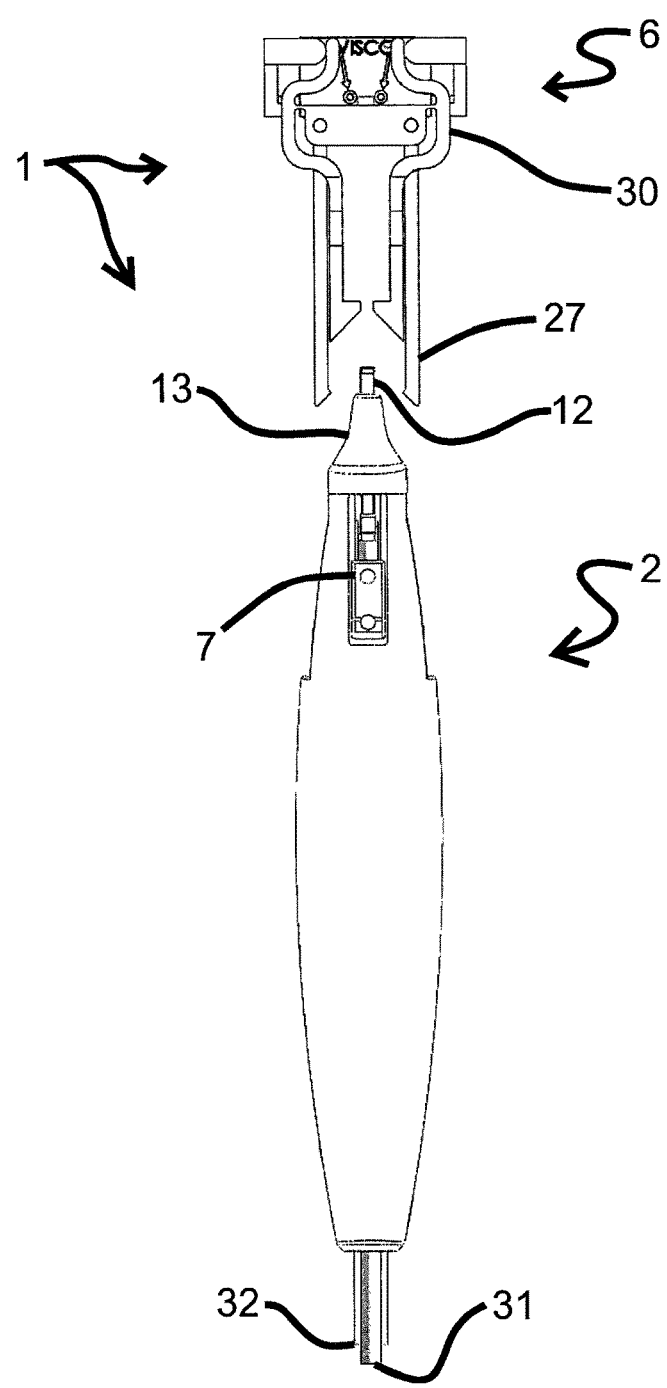
FIG. 8 is a top view of the microsurgery/capsulotomy device and its attachment to a compression chamber, according to an embodiment of the invention.
Figure 8A:
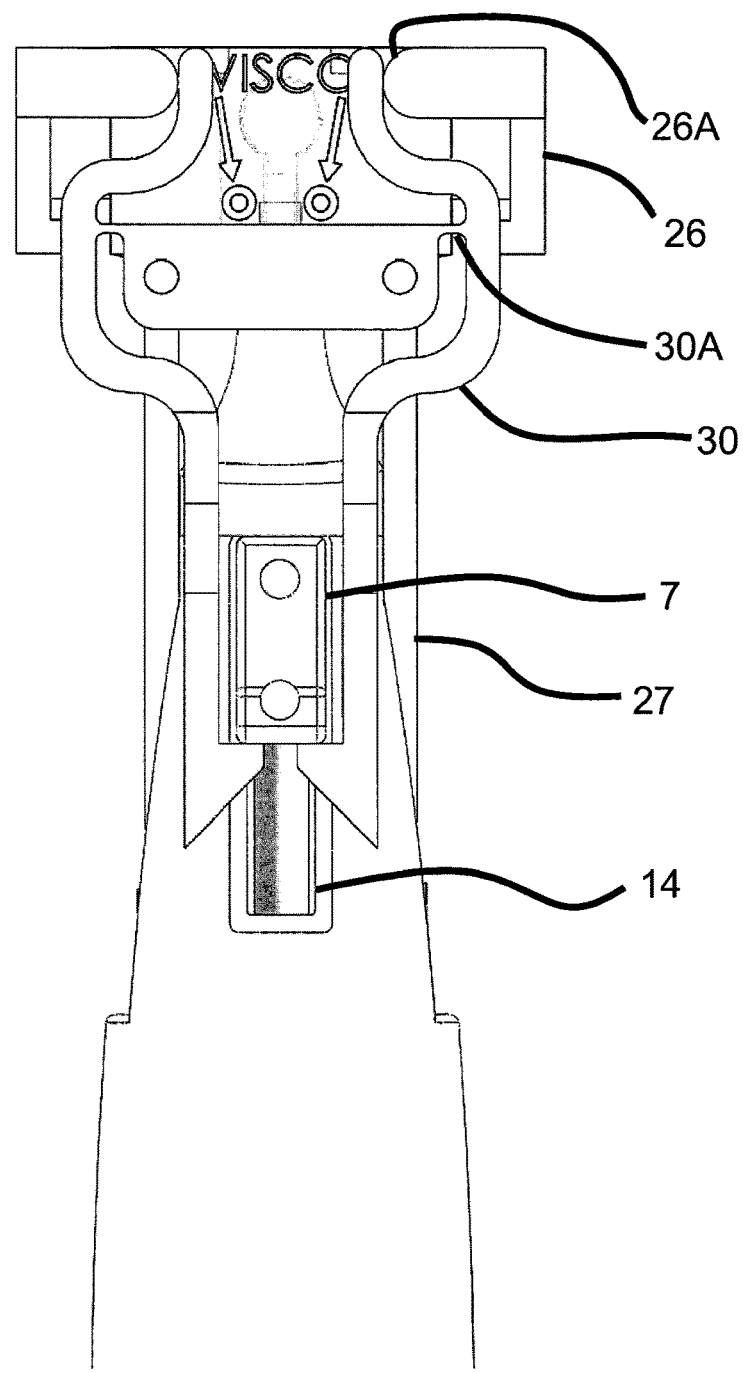
FIG. 8A is a partial top view of the site of attachment of the compression chamber attached to the microsurgery/capsulotomy device, according to an embodiment of the invention.
Figure 8B:
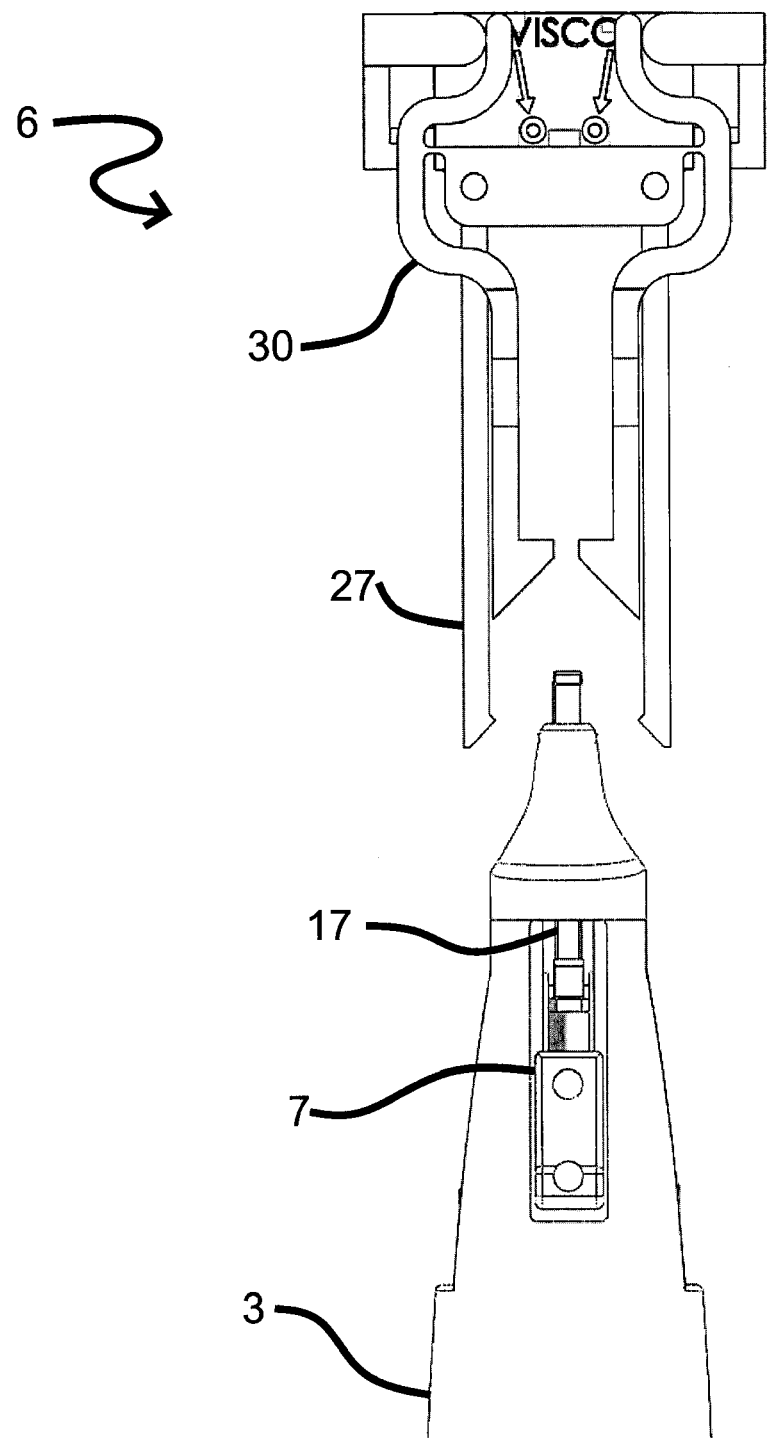
FIG. 8B is a partially exploded top view of the site of the interface between a detached compression chamber and microsurgery/capsulotomy device, according to an embodiment of the invention.

FIG. 7A1 is a side view cross section of a suction cup 16 within a compression chamber. FIG. 7A2 is a top view of the suction cup in an open compression chamber. Side members 26 will be pushed together towards the centerline and to compress the suction cup 16. FIG. 7A3 is a top view of the closed compression chamber 25 with the suction cup pulled into the inserter 12 of the microsurgery/capsulotomy device. FIG. 7B shows a cross-sectional view of the suction cup 16B with a donut shape to apply suction over an annular region of the lens. A cutting element 21 is shown attached to the suction cup.

Figure 10:
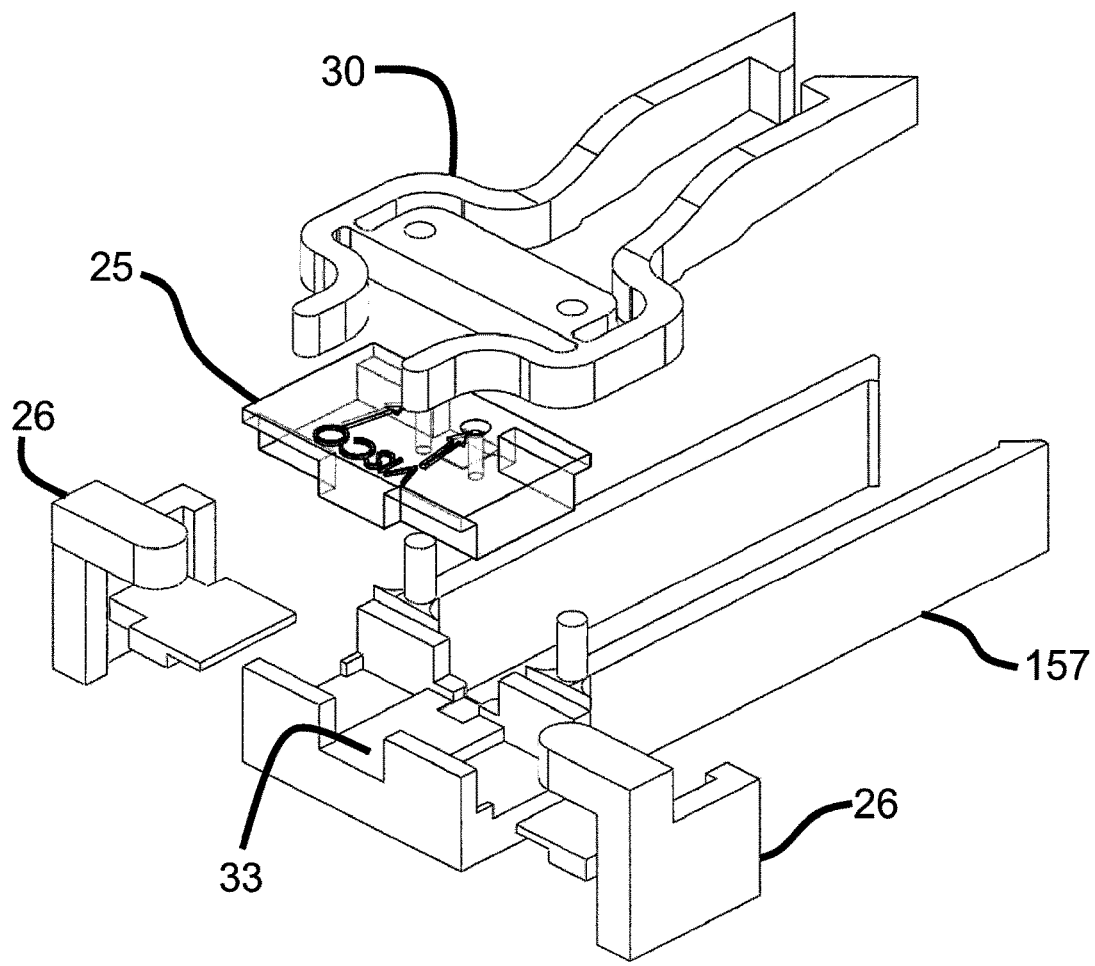
FIG. 10 is a top perspective exploded view of the separate components of the compression device, according to an embodiment of the invention.

FIGS. 8, 8A, 8B, 9, 9B and 10 show an embodiment of the compression chamber 6 having further latching mechanisms 27 to prevent out-of-sequence operation. Latching beams 30 prevent the thumbslide from being slid until after the suction cup has been compressed. In FIG. 10, according to one embodiment of the invention, the roof of the compression chamber is transparent so the user can watch the injection of lubricant (e.g., visco) and the progress of the suction cup compression.

Figure 10B:
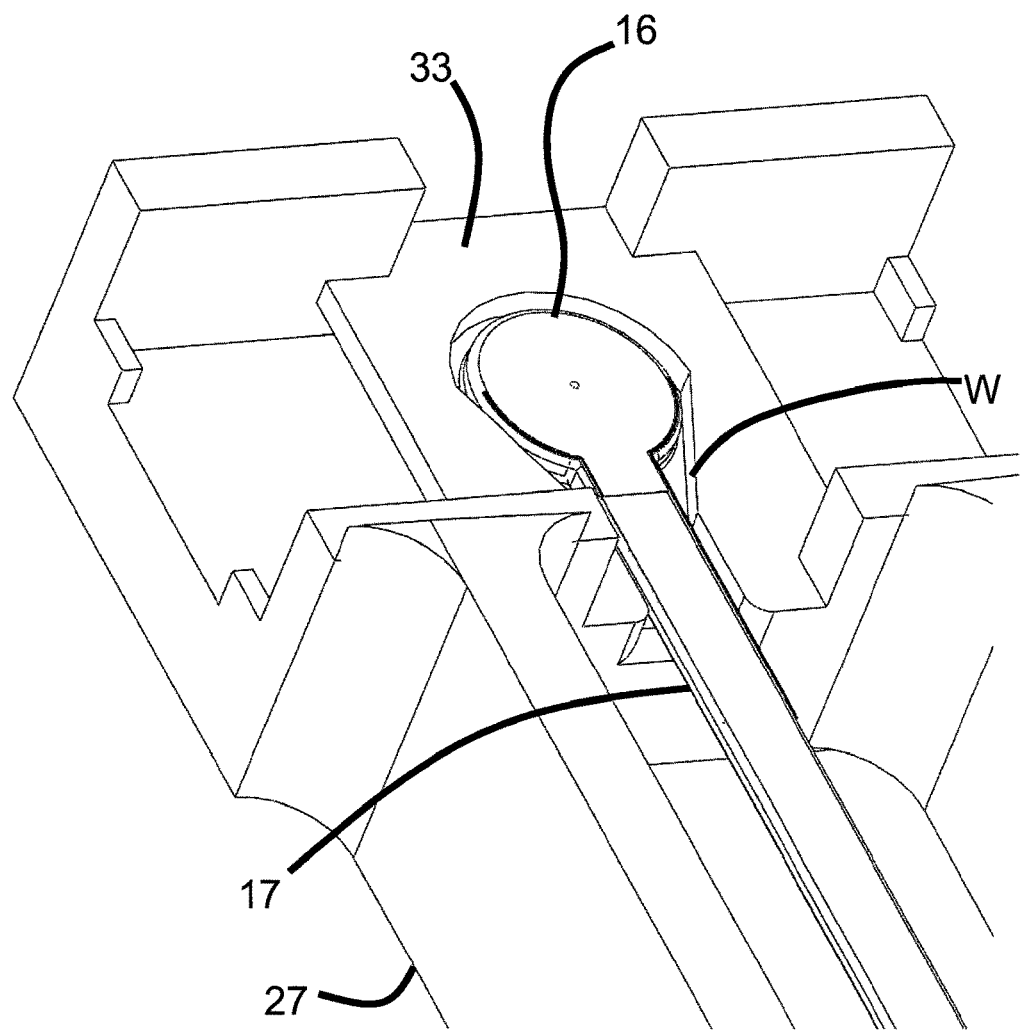
FIG. 10B is an perspective view of the arm and suction cup of the microsurgery/capsulotomy device, within a funnel-like compression device, according to an embodiment of the invention.

FIG. 10B shows a suction cup 16 in a funnel-like compression chamber. Converging sidewalls W, compress the suction cup as it is slid towards and into the inserter (not shown). Compression can be done manually or machine actuated.

Cutting Element and Suction Cup Designs

Figure 11A:
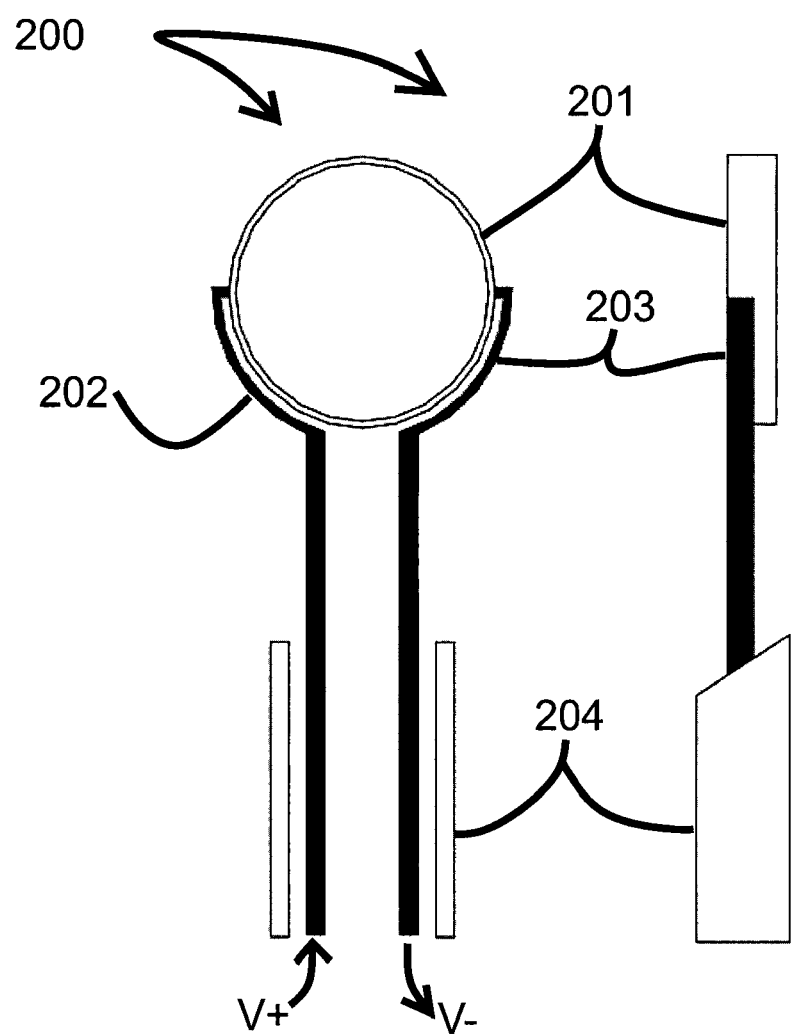
FIG. 11A shows schematic top and side views of a resistive heating device, according to an embodiment of the invention.

In one embodiment, the cutting device comprises an electrode. FIG. 11A shows schematic top and side views of resistive heating device (200). During the electrical pulse, current flows from the V+ supply into lead 202, then through the circular cutting electrode 201, and finally out through lead 203. Since the leads 202 and 203 are joined to electrode 201 at diametrically opposite points on the circle, the resistance to current through each of the semicircular paths around the ring is equal and the current density around the circular electrode is equal. This makes the rise in temperature around the ring equal. The inserter 204 and the suction cup (not shown) do not carry electrical current in this embodiment.

In one embodiment, the electrode 201 dimensions include a width of 10 microns, a height of 500 microns, and a diameter of 5.5 mm. In another embodiment, the electrode 201 material is 304/302 stainless steel. In another embodiment, the leads 202 and 203 are made of high conductivity materials (e.g., copper in the leads) and bring the current to an electrode 201 with a much lower conductivity material (e.g., stainless steel) dissipate more energy at the electrode. In another embodiment, a high conductivity electrode (e.g., gold, or gold copper alloy) is employed so the discharge can be made faster since the total system resistance is less, but more energy may be wasted in the leads to get enough heat at the electrode. In another embodiment, the electrode 201 is sufficiently thin and elastic to avoid plastic deformation during use. In one embodiment, suitable alloys for the electrode include 304/302 stainless steel, beryllium-copper, copper-gold, and many other well-known spring alloys.

In one aspect, the leads are 75 micron diameter wire. In another embodiment, the leads are made of copper that is plated with nickel. This will facilitate spot welding on to a stainless electrode and a stainless steel stem structure. In another aspect, the inserter is made of material that is 50 microns thick. In still another aspect, the inserter is made of 304/302 stainless sheet.

FIGS. 11A2, 11A3, 11A4 show an electrode design 300 in which metallic conductors 303, 304, 305, 306 are sputtered and/or plated on a flexible insulating support (e.g., Kapton, polyimide), and bonded to leads 302 and 307. In one embodiment, the current flow is via lead 302 into ring 303 located on the outer dimension (i.e., "OD") surface of support ring 301. Half the current goes clockwise, and half goes counterclockwise 180 degrees around the ring to distal bridge conductor 304 to ring 305 located on the inner dimension (i.e., "ID") surface of support ring 301, and again half the current flows clockwise and half flows counter clockwise around the ring, then through proximal bridge conductor 306 to lead 307. This current path is shown by arrows 302A, 303A, 303B, 304A, 305A, 305B, 306A, 307A. FIG. 11A3 shows that the bottom edge 301A of the insulating support ring 301 does not have conductive material. FIG. 11A4 shows that the only connection between conducting rings 303 and 305 is at the distal bridge conductor 304. This geometry results in an equal current density everywhere along the electrode edges that contact the membrane. It also places the leads 302, 307, on the centerline so they are not affected by the compression step needed to fit through the corneal incision. In one embodiment, the leads are straight and built into the suction cup. In one embodiment, the electrode is in the shape of a Kapton ring with wall thickness of about 25 microns, wall height of about 500 microns, and a diameter of 4.5 to 6.0 mm. In another embodiment, the electrode comprises sputtered/plated metal (e.g., nickel, gold, alloy) 5 to 15 microns thick, and the lead wires are made from, e.g., copper, gold, nickel, alloy, and are 50 microns to about 100 microns in diameter. The strategy of using an insulating support (e.g., Kapton) can be applied to any of the electrode geometries.

Figure 11B:
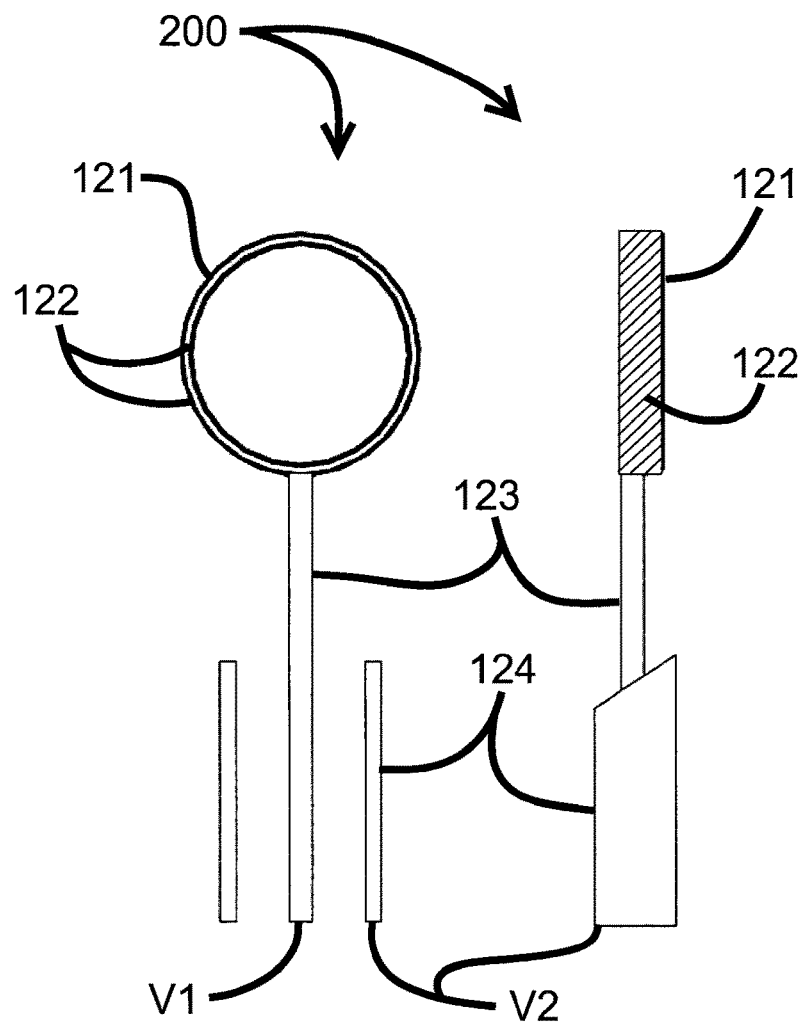
FIG. 11B depicts top and side views of a current focusing device, according to an embodiment of the invention.
Figure 11C:
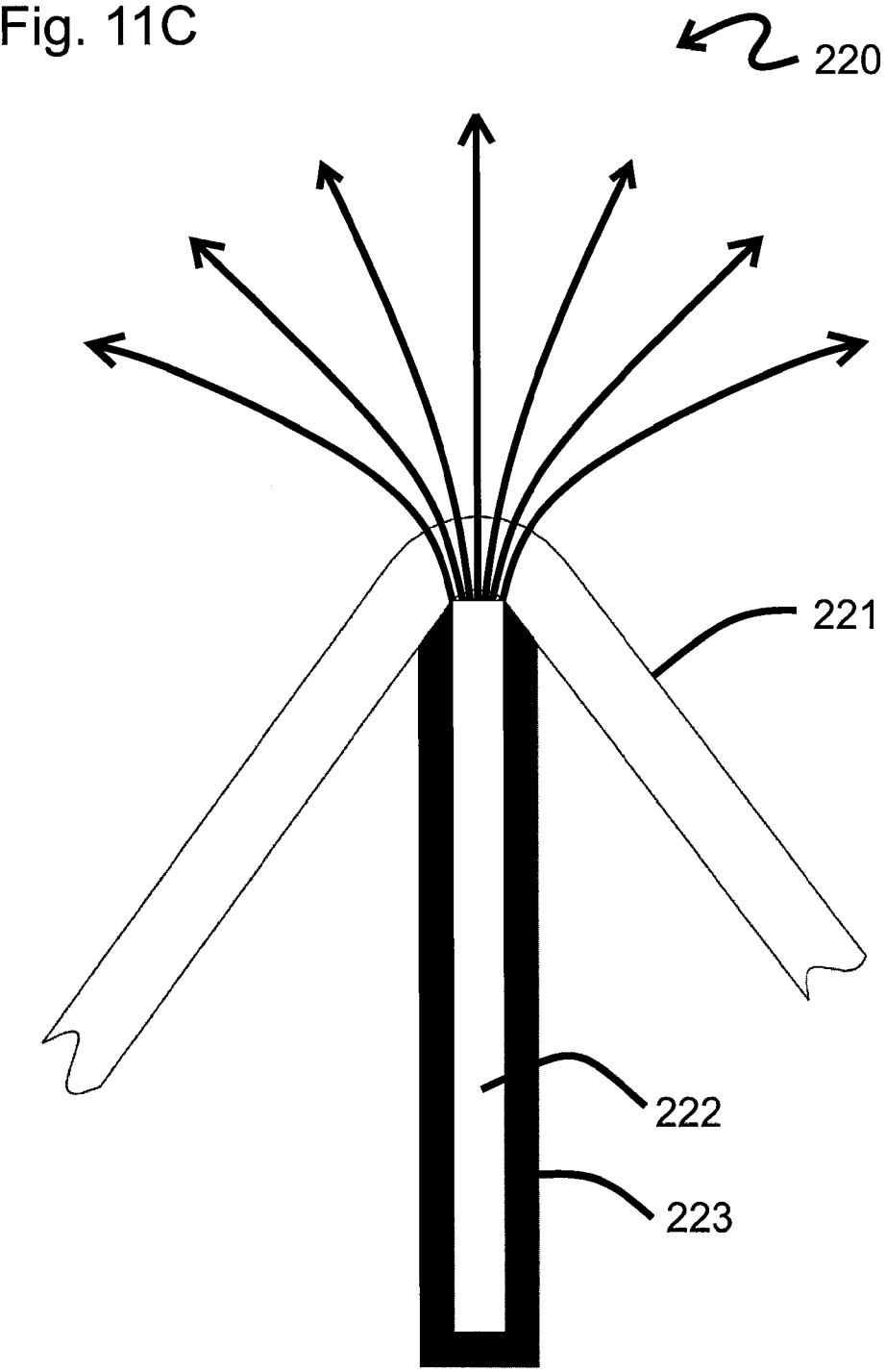
FIG. 11C depicts electric field lines through a capsular membrane stretched over an electrode, according to an embodiment of the invention.
Figure 11D:
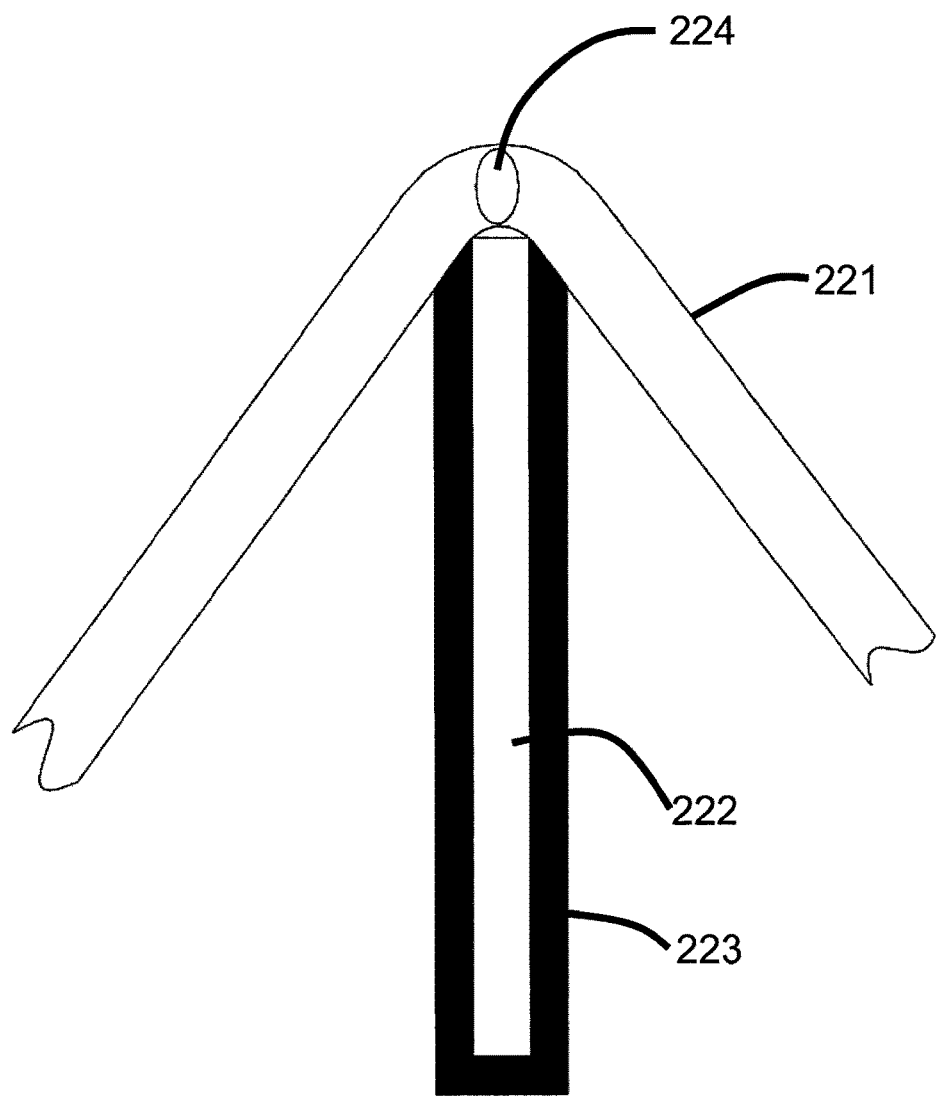
FIG. 11D depicts the formation of a rupture in a capsular membrane stretched over an electrode, according to an embodiment of the invention.
Figure 11E:
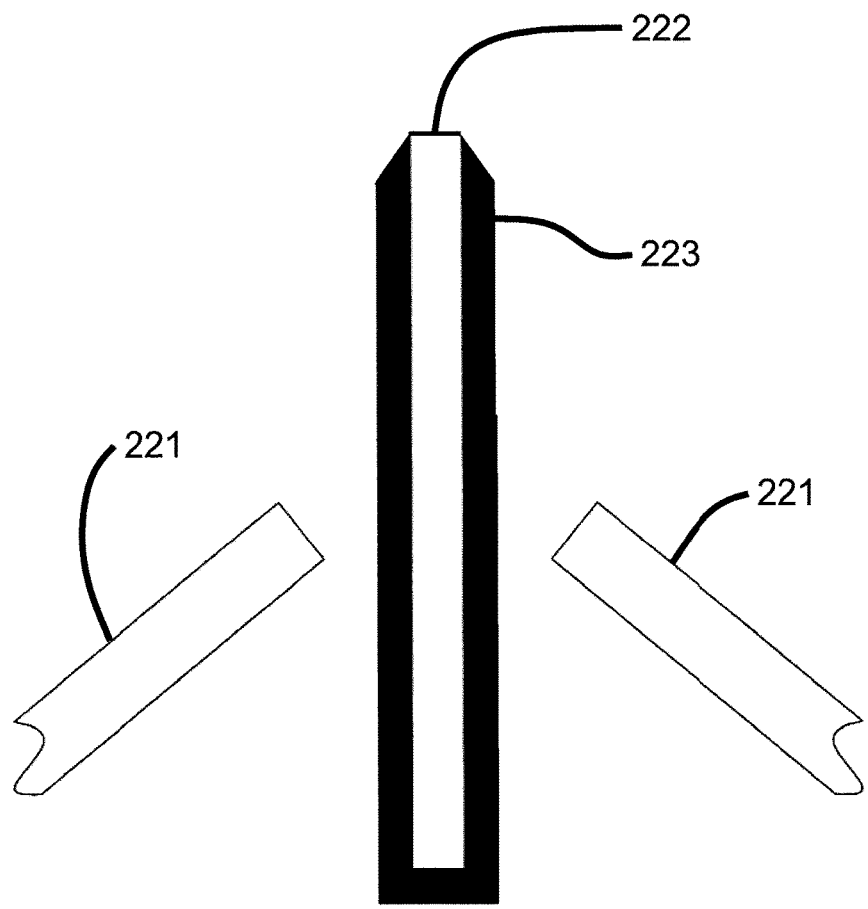
FIG. 11E depicts a cut membrane after the cutting event is done.

FIG. 11B shows schematic top and side views of a current focusing device 120. During the electrical pulse, current flows from the V1 supply into lead 123 and into the circular electrode 121, and then from the uninsulated edge of 121 into the tissue and on to the return electrode which is inserter 124. Insulating material 122 covers the rest of the electrode, and lead 123 is also insulated. Because the exposed metal at the edge of electrode 121 has a small area, the electric field strength and the current density are both high for a distance of 10 to 30 micrometers out from the electrode surface. Since the capsular membrane is being sucked forcibly over this exposed metal edge and has a thickness of about 10 to 30 microns, high current density and its resulting heating will extend through the thickness of the membrane and will be confined to the circular path which is already under applied tensile stress by suction, and the membrane will be cut along this circle. Depending on the applied voltage and duration of the pulse (e.g., >600V for 100 microseconds (or less)), a micro plasma forms to directly break atomic and molecular bonds in the cutting path, and/or the thermally activated volume expansion of the membrane tissue in the current path increases the stress within the membrane to a level that causes it to rupture over the circular path. More than about 30 microns from the electrode edge, the divergence of the current is great enough that the current density is too low to damage tissue. Finally the return electrode (inserter 124) has a very large surface area so the current density there is low. For AC (radio wave or microwave) discharges, current directions are reversible, but the current pathways and geometric focusing remains the same as a DC pulse. FIG. 11C shows the capsular membrane 221 stretched by suction over the electrode 222. When current flows from the electrode to the tissue it follows the electric field lines 220. Insulation 223 prevents current flow from anywhere else on the electrode other than the exposed bare metal edge as shown. FIG. 11D shows the instant after the formation of a rupture 224 within the membrane due to the focused current pulse. FIG. 11E shows the cut membrane after the cutting event is done. For the current focusing strategy, the same electrode materials mentioned above (e.g., copper, gold, nickel, or alloys) can be used.

Figure 12:
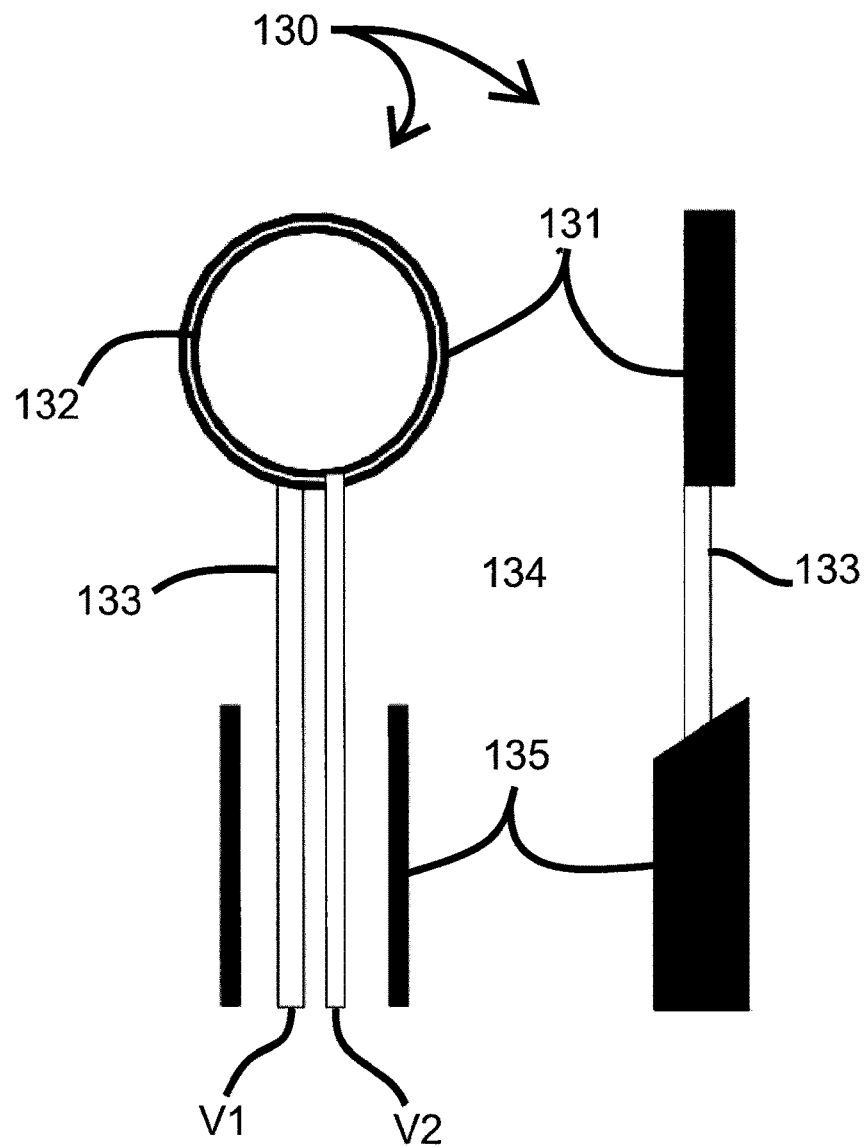
FIG. 12 is a top and side view of a current focusing device having two concentric electrodes, according to an embodiment of the invention.

FIG. 12 shows another current focusing device 130 with two concentric electrodes 131 and 132. Both electrodes are insulated except at the very narrow edge that is pressed against the capsular membrane. In this case both the source and return electrodes are focusing the current to a high current density, and the entire current path is substantially constrained to lie within the thickness of the membrane, and to the circular path of desired cutting. During the flow of electrical current pulse (which may be a DC or AC pulse) the current path elements are lead 133, outer circular electrode 131, membrane tissue, inner circular electrode 132, and second lead 134 (each lead is connected to only one of the circular electrodes). The inserter 135 and suction cup (not shown) do not carry current in this design.

Water molecules trapped adjacent to the circular electrodes could be electrolyzed to produce a small bubble of hydrogen and oxygen, then a high voltage pulse could induce a spark jump between the electrodes to ignite the bubble and generate enough stress to cut the membrane along the circular path. In one embodiment, a thin coating of platinum or palladium on the electrodes would help in the formation of hydrogen gas. In one embodiment, the electrode configuration of FIG. 12 is used for this method of cutting.

After the electrical pulse cuts the circular patch of capsular membrane, the patch must be removed for the eye. There are several strategies that would enable the device itself to do this.

Figure 13:
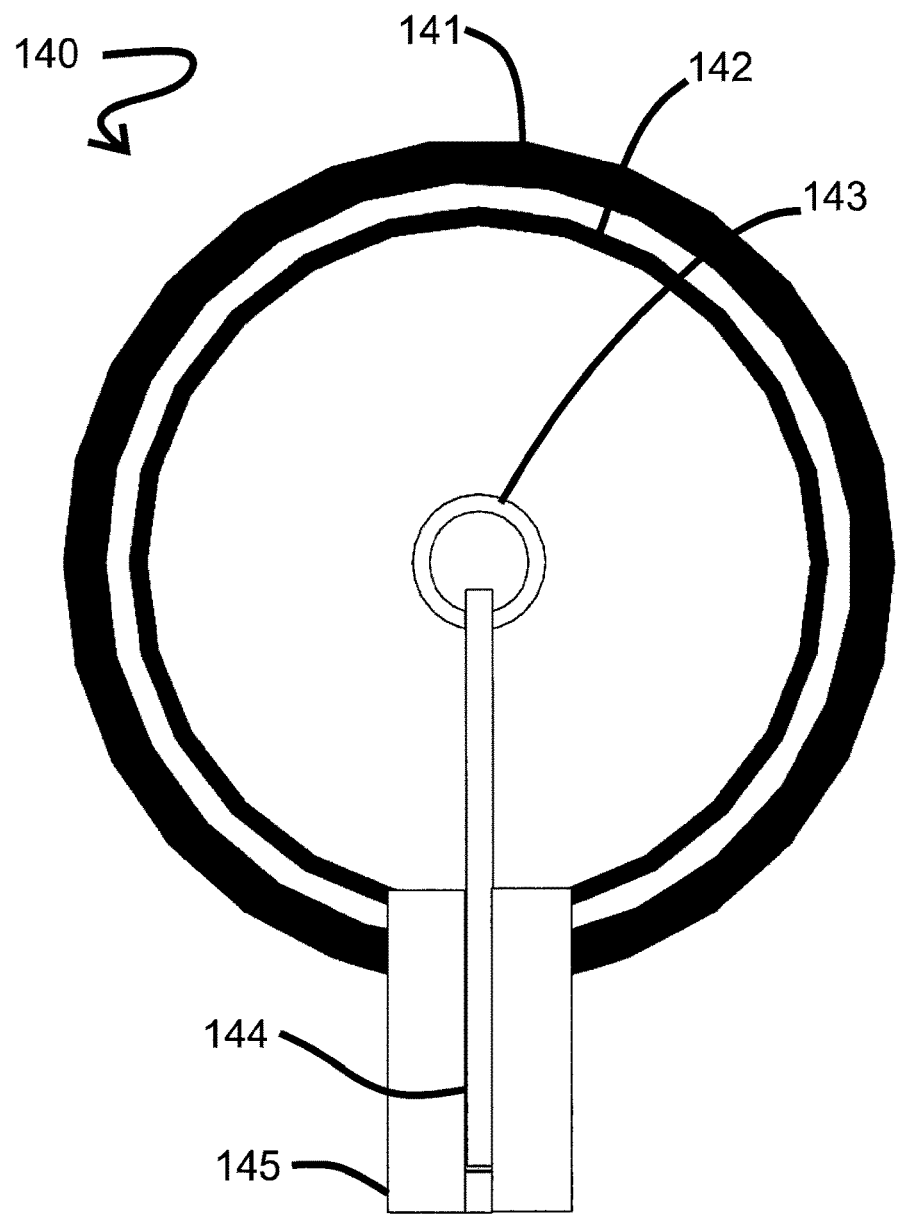
FIG. 13 is a top view of a device having a suction cup that makes contact with the lens over the annular area, according to an embodiment of the invention.

FIG. 13 shows a schematic top view of a device 140 having a suction cup that makes contact with the lens over a first annular area 141. A circular electrode 142 makes uniform 360 degree contact with the capsule. Fluidic connection to the suction cup by means of tubulation 145 allows fluid to be withdrawn from the volume that lies within the ID of the first annular area 141. Tubulation 145 also allows fluid to be injected into the volume that lies within the ID of the first annular area 141. There is a microsuction cup located within the volume enclosed by the suction cup. The microsuction cup contacts the lens over a second area 143 and can apply suction over the volume within the ID of the second area 143. A small diameter tube 144 allows fluid flow into or out of the microsuction cup independently from the fluid flow into or out of the larger suction cup.

In use, after the device is inserted into the anterior chamber of the eye, and located on the optical axis of the lens, or any suitable location, suction is applied to the suction cup and to the microsuction cup to force them against the lens capsule. Then the electrical pulse is discharged through the electrode 142. Then fluid is pumped into the suction cup through tubulation 145 to eliminate the force holding it against the lens, and during this time suction is still being applied to the microsuction cup through tube 144 to hold on to the excised patch of capsular membrane. It is possible that the excised capsule membrane patch may be sucked into tube 144. The fluid flow into 144 is less than the fluid flow out of 145 (i.e. fluid going into the suction cup to eliminate suction), so the device as a whole still releases from the lens. It is also possible that the patch may stay in the microsuction cup and block further fluid flow into 144. In either case, the excised patch remains attached to the device and is removed from the eye when the device is removed from the eye. In one embodiment of the invention, multiple microsuction cups are positioned at suitable locations on the underside of the large suction cup and utilized to capture the excised capsule membrane.

Figure 14:
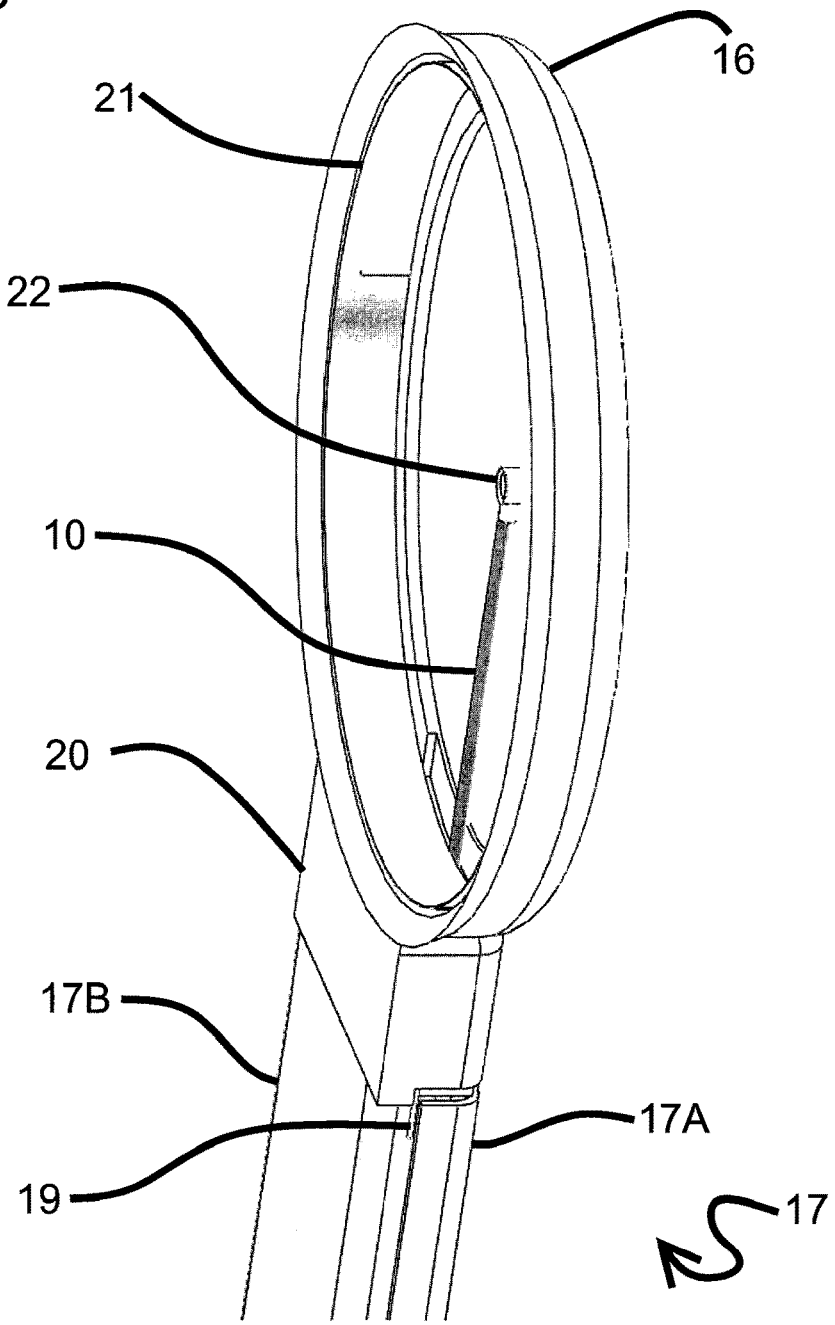
FIG. 14 is an underside perspective view of a suction cup having a microsuction cup inside it, according to an embodiment of the invention.
Figure 15A:
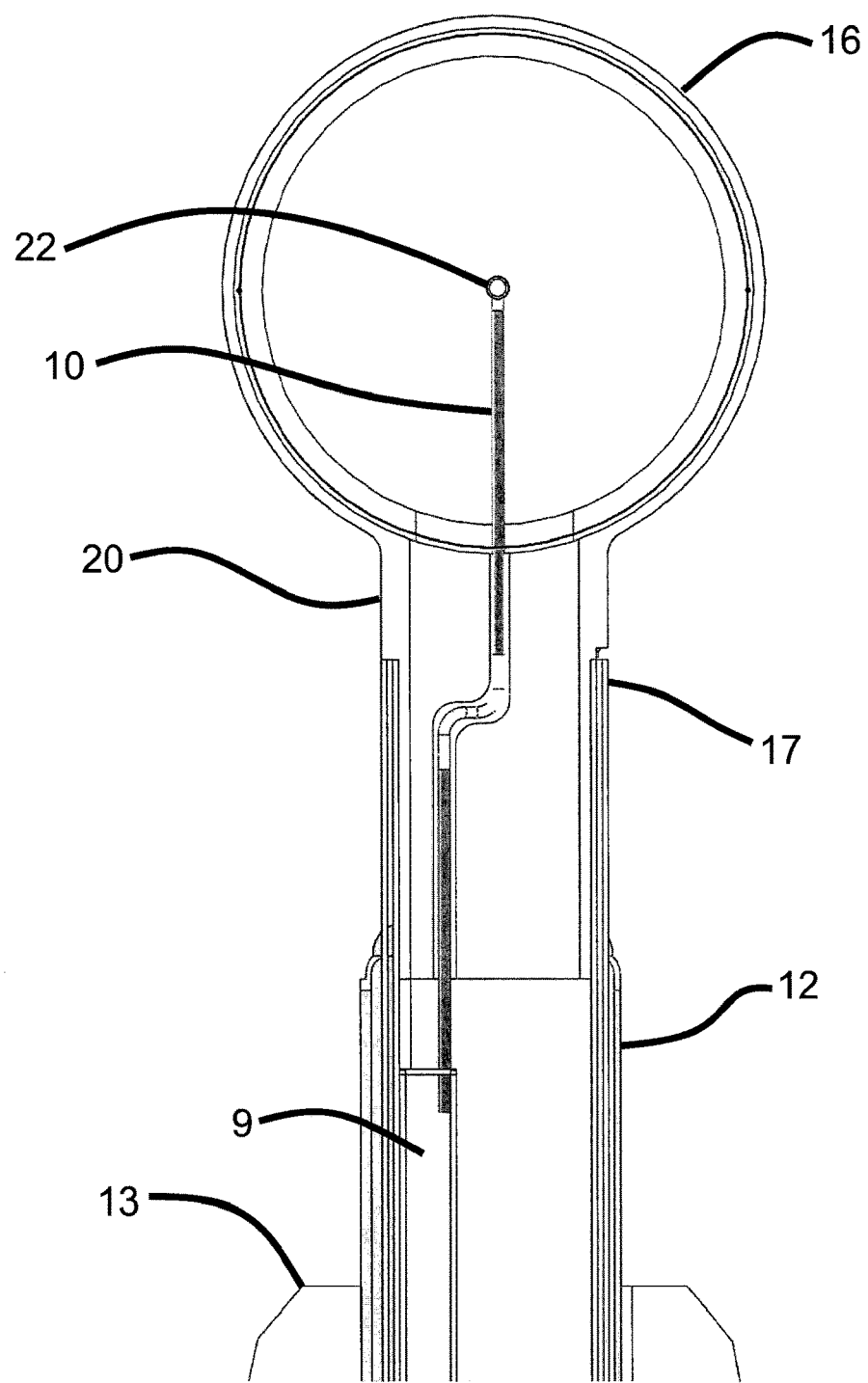
FIG. 15A is a cutaway view of the microsurgery/capsulotomy device depicting how the two suction cups are fluidically independent, according to an embodiment of the invention.
Figure 15B:
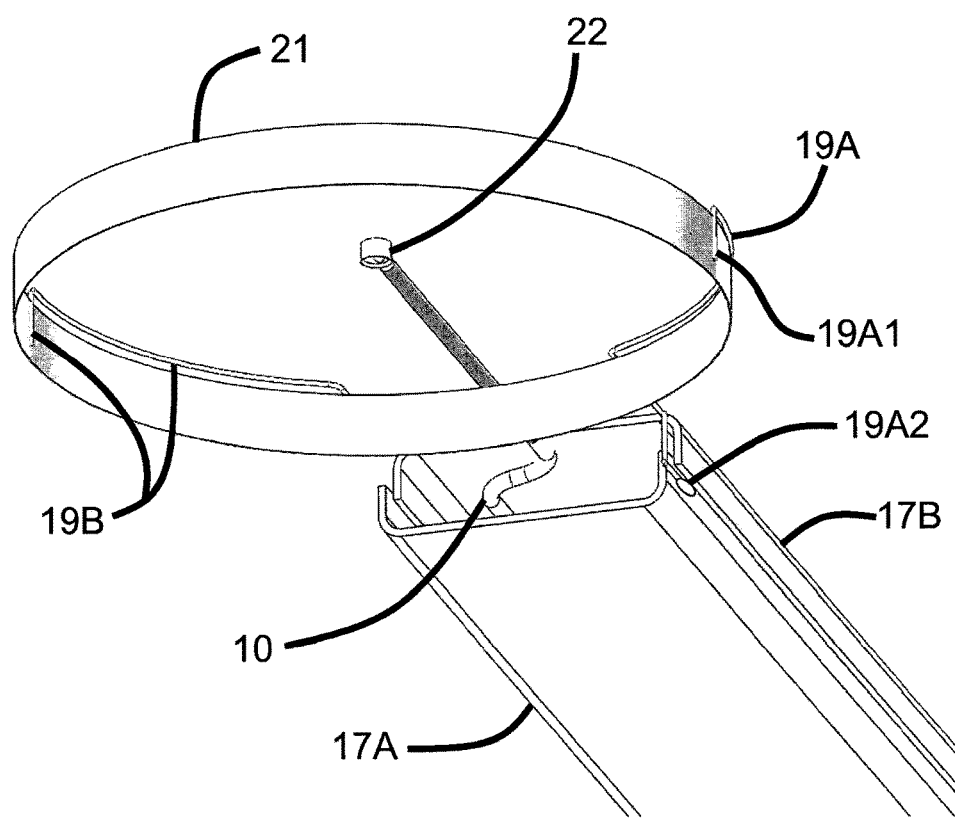
FIG. 15B is a cutaway view of the microsurgery/capsulotomy device with the suction cup removed, according to an embodiment of the invention.
Figure 16:
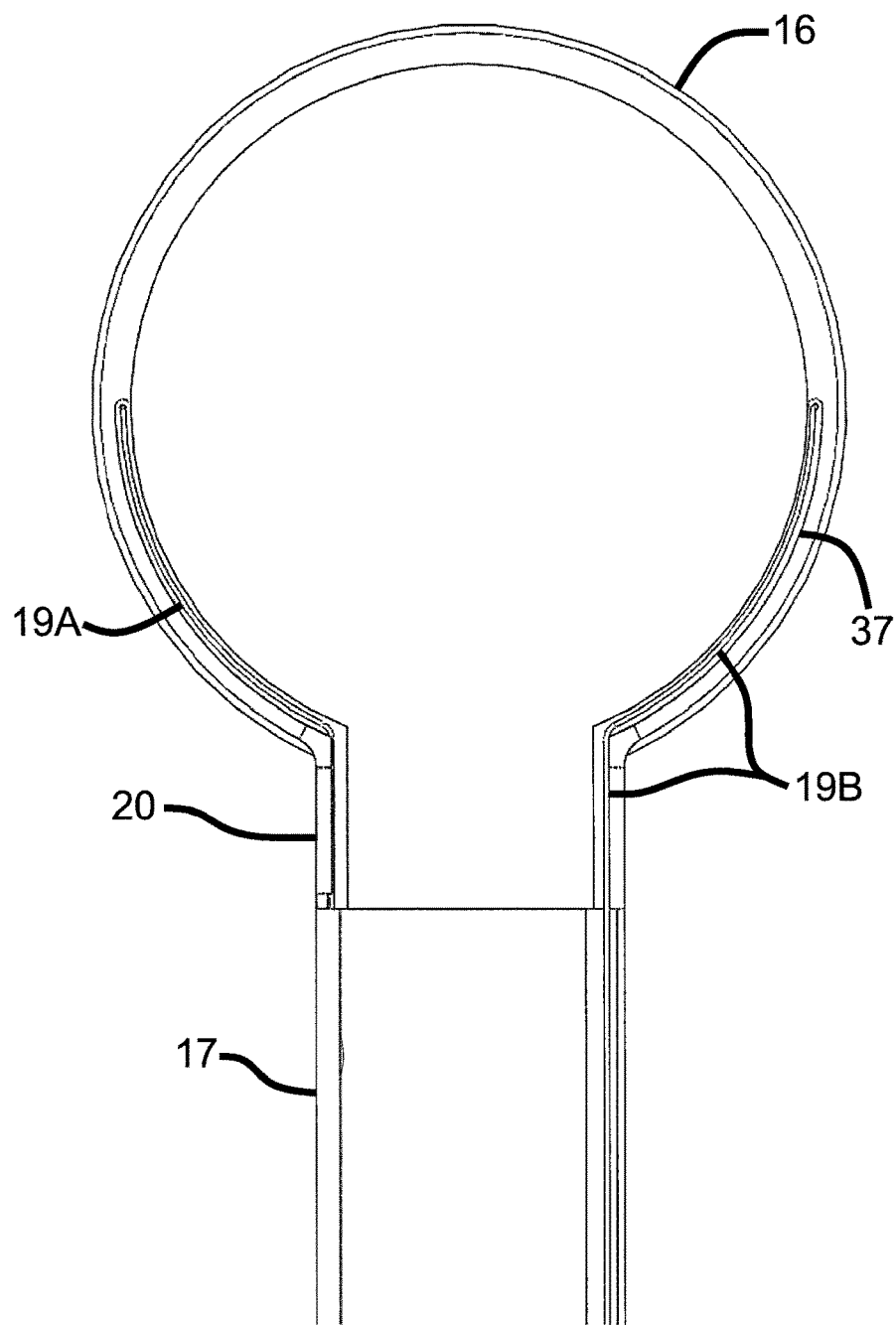
FIG. 16 is a top view of the suction cup, according to an embodiment of the invention.
Figure 17:
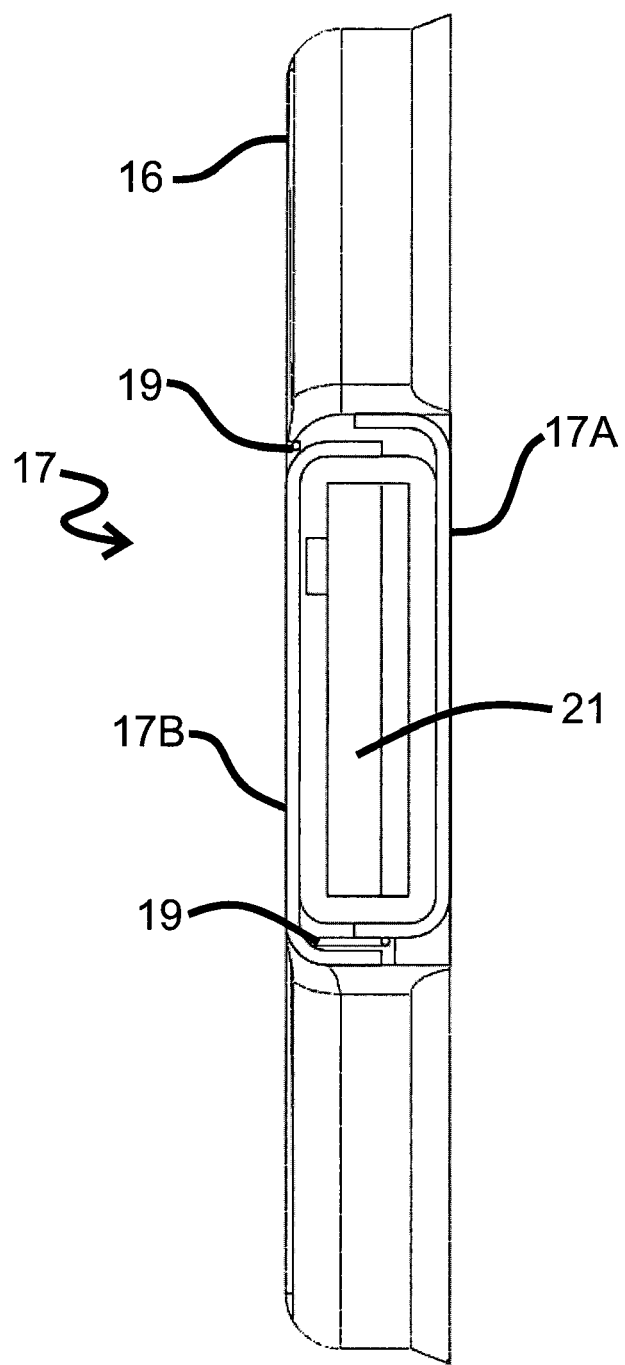
FIG. 17 is an end view of stem components, according to an embodiment of the invention.

FIG. 14 shows a view for the underside of a suction cup 16 having a microsuction cup 22 inside it. Tubulation 20 allows fluid flow into or out of suction cup 16. Tube 10 allows independent fluid flow into or out of microsuction cup 22. Stem 17 comprises two conductors 17A and 17B that are electrically insulated from each other. Electrode 21 is electrically connected to stem components 17A and 17B by leads 19A and 19B (see FIG. 15B). FIG. 15A shows a cut away view that reveals how the two suction cups are fluidically independent. In this example the small tubing 10 for the microsuction cup 22 lies within the lumen of the tubing for the large suction cup. FIG. 15B shows the components of the microsurgery/capsulotomy device without the suction cup present. Circular electrode 21 is welded to lead 19A and 19B. In one method, weld 19A1 is made by electrically (or by laser) spot welding nickel plated copper wire 19A to 10 micron thick stainless steel electrode 21, and weld 19A2 is made by spot welding the other end of lead 19A to the stainless steel stem component 17B (note that the insulating material coating 17B is not shown here for clarity). FIG. 16 shows a top view of the suction cup 16. Leads 19A and 19B connect to diametrically opposite points on the circular electrode inside the suction cup, and to insulated components of the stem 17. FIG. 17 shows an end view of stem components 17A and 17B. Part of electrode 21 is visible through the lumen of the stem and suction cup tubulation.

Figure 18:
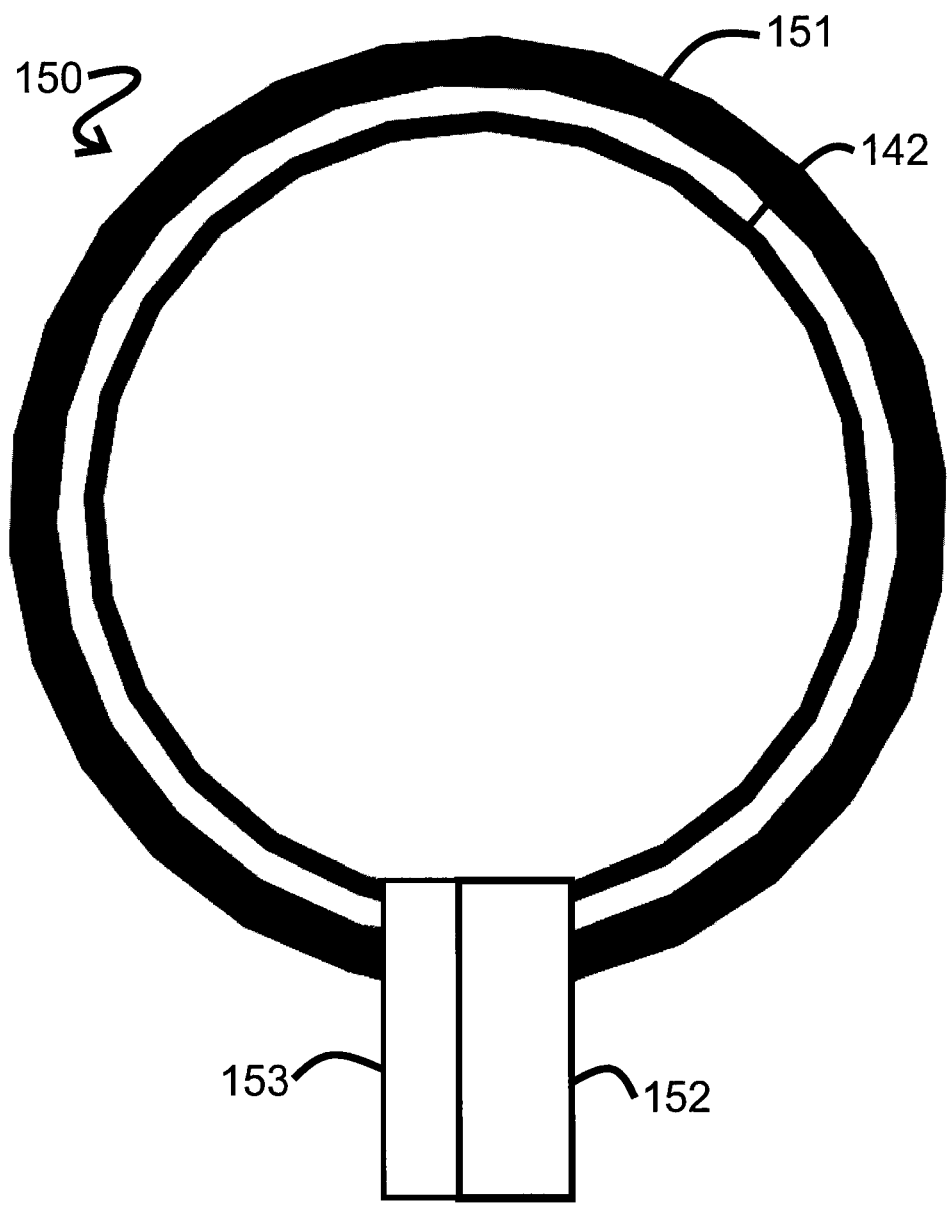
FIG. 18 is a top view of the microsurgery/capsulotomy suction cup, according to an embodiment of the invention.

FIG. 18 shows a schematic top view of a device 150 having a suction cup that contacts the lens over an annular area 151. The tubulation for fluidic conduction into and out of the interior of the suction cup has two lumens 153 and 152. The two lumens can operate independently with one injecting fluid into the suction cup while the other withdraws fluid. Thus a flushing action can be established within the suction cup that will flush out the excised patch of membrane. In a preferred embodiment, the fluid for flushing would be a low viscosity solution that will not harm the living cells in the eye in the event that any leakage out of the suction cup should occur. Note also that both lumens can be used to provide suction at the same time. In one embodiment, both lumens inject fluid at the same time.

Figure 19:
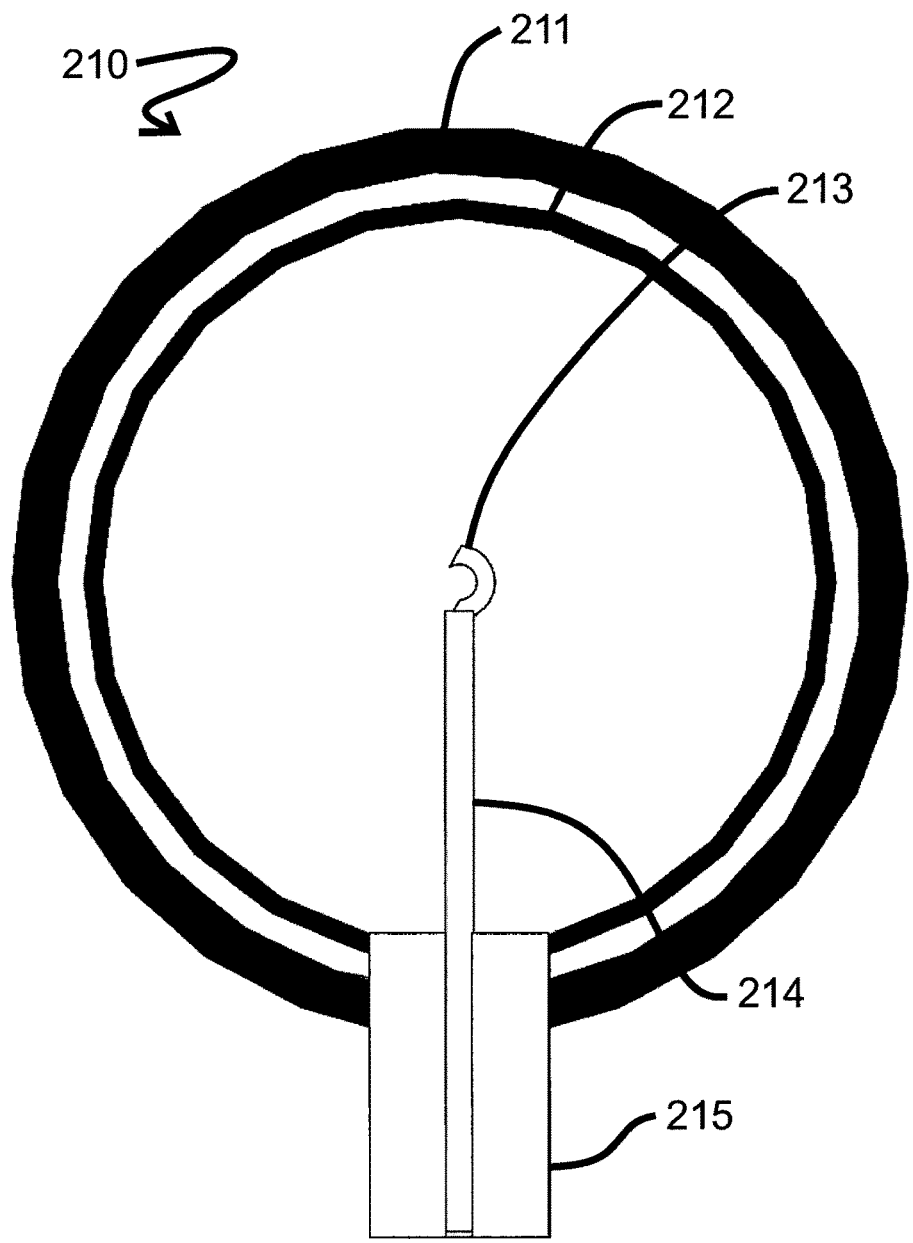
FIG. 19 is a top view of another design of the microsurgery/capsulotomy device having a microhook slidably mounted within a suction cup, according to an embodiment of the invention.

FIG. 19 shows a schematic top view of a device 210 having a microhook 213 that is slidably mounted within a suction cup. The suction cup contacts the lens over an annular area 211. Lumen 215 can provide suction or fluidic injection. After the electrical pulse through electrode 212 cuts the capsular membrane, the shaft 214 with the microhook 213 on the end can be slid back into the lumen of tubulation 215. Shaft 214 is pre-bent slightly downwards so that it will automatically press the microhook against the capsular membrane. The microhook 213 is assembled with the orientation needed so that its point will dig into the membrane as the shaft 214 is withdrawn. This will take the patch of membrane out of the eye. Note that it is not necessary to have shaft 214 slidably mounted, it can be fixed to the suction cup, and since it is pre-formed to bend against the capsule, when the device is removed from the eye the microhook will dig into the capsule patch and pull it out.

In one embodiment, the device may have hooks or barbs that don't have independent movement means, but are anchored to the suction cup and get compressed downwards when suction is applied, so hooks and/or barbs puncture the capsule and drag it out when the device is pulled out of the eye.

Other Microsurgery/Capsulotomy Device Designs

Figure 20:
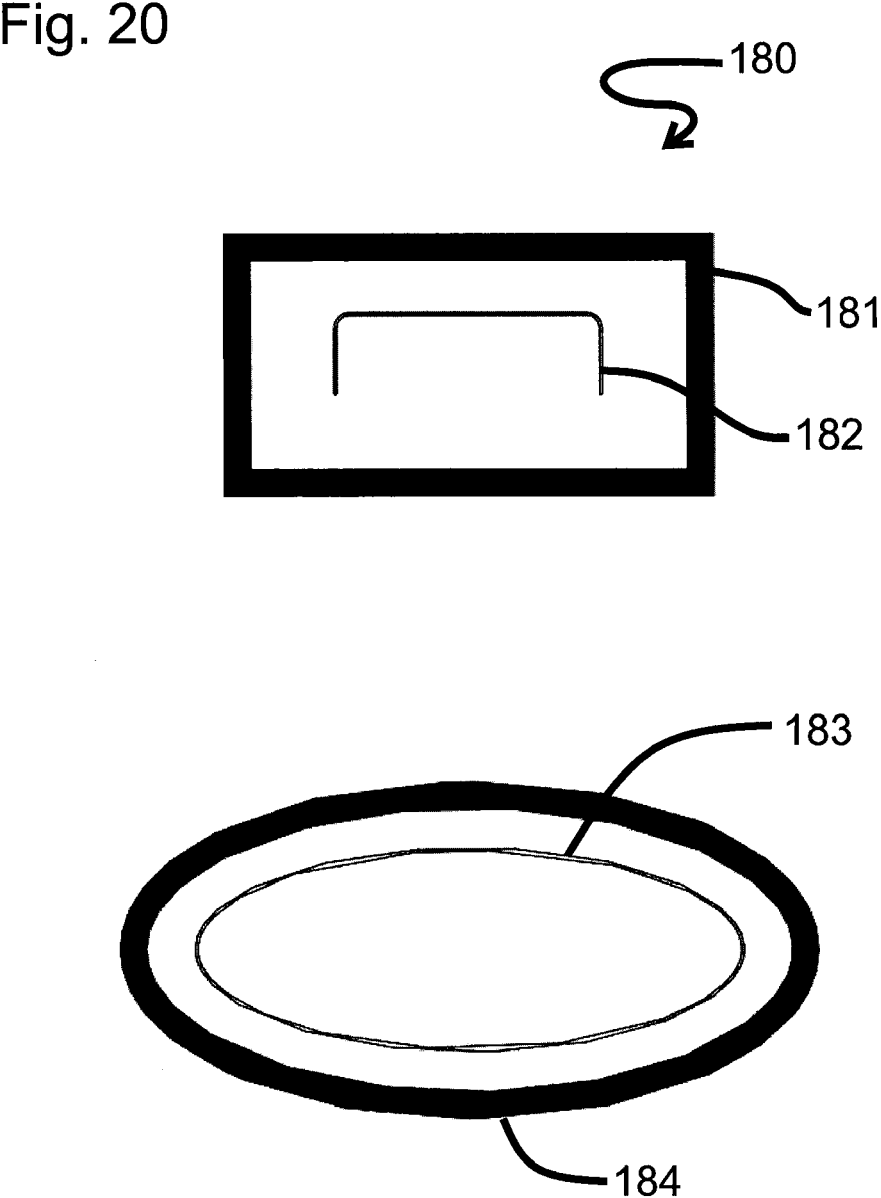
FIG. 20 is an end perspective view of other configurations of the electrode, according to an embodiment of the invention.

FIG. 20 shows end views of some possible configurations of current focusing microsurgical devices 180. The surrounding suction tube may be a closed curve of any shape, for example a rectangle 181 or an ellipse 184. The current focusing electrode that lies within the lumen of the suction tube defines the cutting path, and may be an open curve or a closed curve. The cutting path 182 forms a flap of tissue that remains attached on one edge. The elliptical cutting path 183 would be used to excise an elliptical patch from a membrane.

Figure 21:
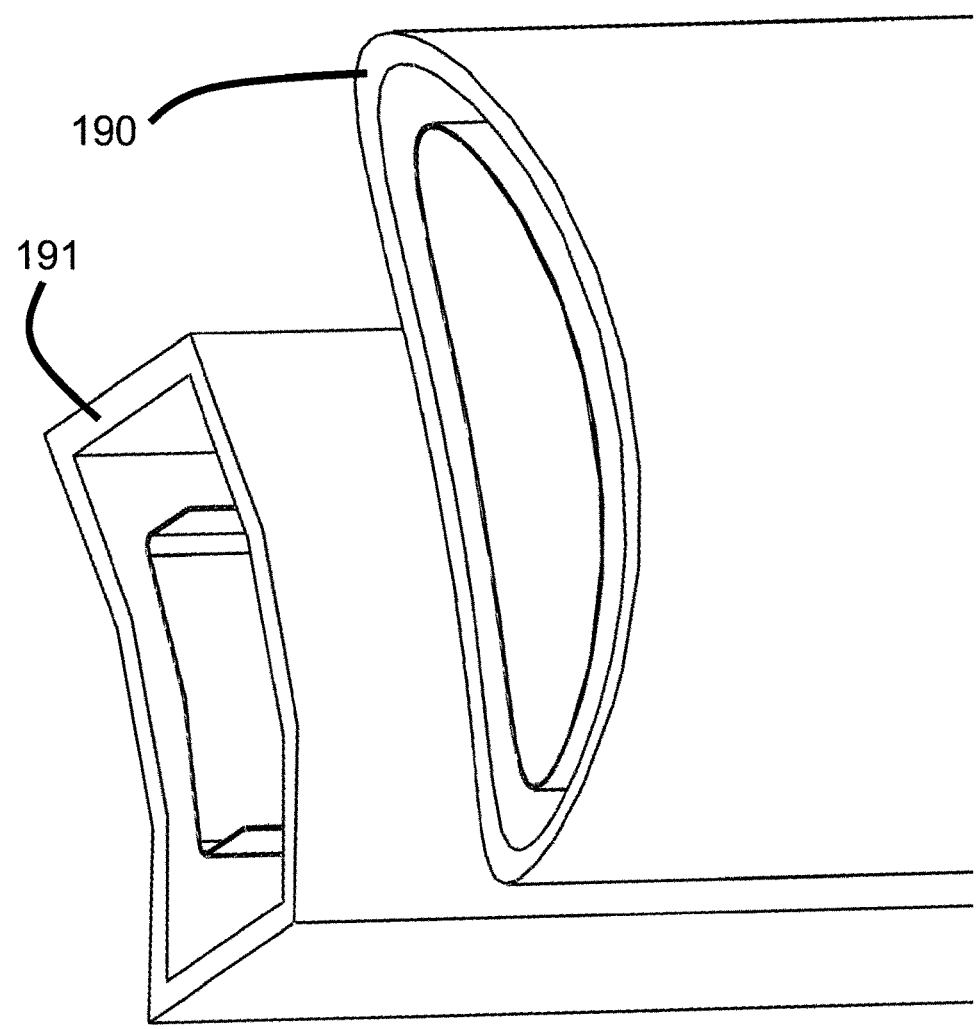
FIG. 21 is an end perspective view of configurations of the face of the electrode and suction tube, according to an embodiment of the invention.

FIG. 21 shows that the face of the suction tube and electrode do not have to lie in a plane. They may be shaped to fit securely against the 3 dimensional tissues they are to operate on. For example they may fit against a cylindrical optic nerve of radius 1.5 mm and perform a microfenestration operation through the membrane that confines the bundle of retinal axons to provide fluidic pathways to reduce the hydrostatic pressure therein.

In one embodiment, the microsurgical structure is simply an electrically conducting tube that is coated with an insulator wherever current flow into tissue is not desired, and one or more orifices having bare metal edges where cutting is desired. An orifice may be at the end of a tube, or on the side of a tube.

As shown in FIGS. 22 A-C an electrically conducting tube 241 of arbitrary cross sectional size and shape is coated everywhere with electrically insulating material 243 except where cutting is desired 242 and bare metal is exposed. In FIG. 22A the cutting orifice is brought into proximity with the membrane or tissue 240 to be cut. In FIG. 22B the suction is applied to the lumen of the tube causing a distension or bulge 244 of the tissue into the orifice. FIG. 22C shows the result after the electrical pulse has been applied to sever the bulge of tissue and the severed tissue 246 is sucked into the tube.

FIGS. 22.1 A-C shows cross sections of an embodiment similar to FIG. 22 except that instead of a remote return electrode, the return path for the current is via an electrode 246 that is located within the lumen of electrode 241. Again, insulating material 243 covers all conductors except where current flow to or from tissue is desired. FIG. 22.1B shows suction applied to force tissue into the lumen, and FIG. 22.1C shows excised tissue after electrical discharge has occurred. Since the return electrode 264 is closer to the current focusing (tissue cutting) electrode, lower voltages can be used than in the devices having a remote electrode for return current.

Figure 23:
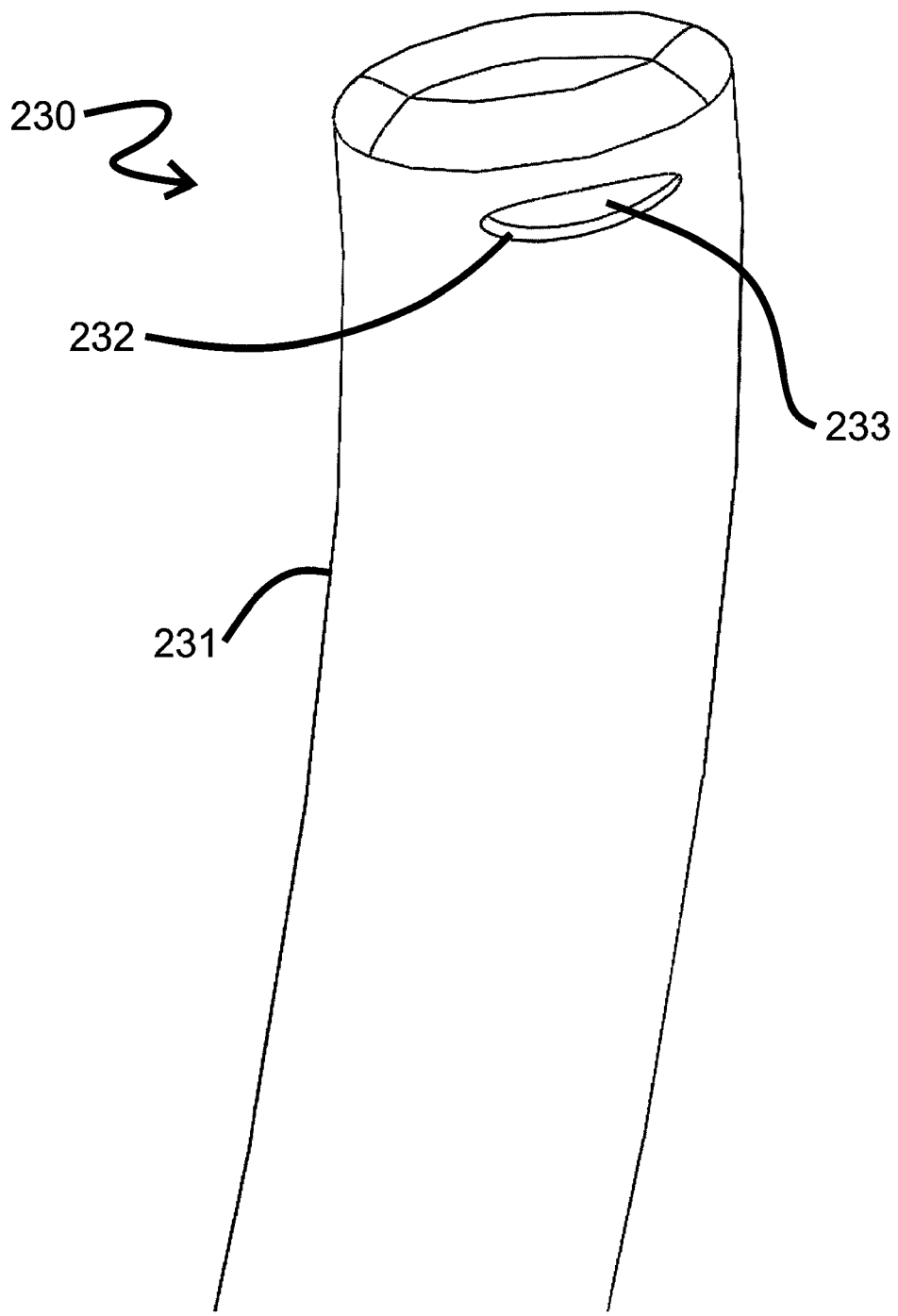
FIG. 23 depicts a current focusing microsurgical device having a shape and size that allows it to fit inside Schlemm's canal, according to an embodiment of the invention.

FIG. 23 shows a current focusing microsurgical device 230 having a shape and size that allows it to fit inside Schlemm's canal. It consists of a metallic tube 231 made from a good electrical conductor (e.g., Cu, Au, or an alloy Cu with Au, or other elements, if special mechanical properties (e.g., more hardness) are desired) having an orifice 233 on the side of the tube confronting the trabecular meshwork. A thin coating of an electrically insulating material prevents current flow out of the metal everywhere except at the bare metal of the edge 232 of the orifice. When suction is applied to the lumen of the tube, trabecular tissue bulges into the lumen of the tube, through the orifice and is placed in a state of tensile stress. Then a high voltage pulse of short duration (e.g., 600V for less than about 100 microseconds) causes a high current density to flow through the tissue at the edge of the orifice and sever it. The suction force moves the severed tissue further into the lumen of the tube, and newly exposed tissue bulges into the lumen. Further cutting can be repeated at the same location, or the suction force can be reduced enough that the tube can be slid further around Schlemm's canal to the next point where a cut is desired.

Figure 24:
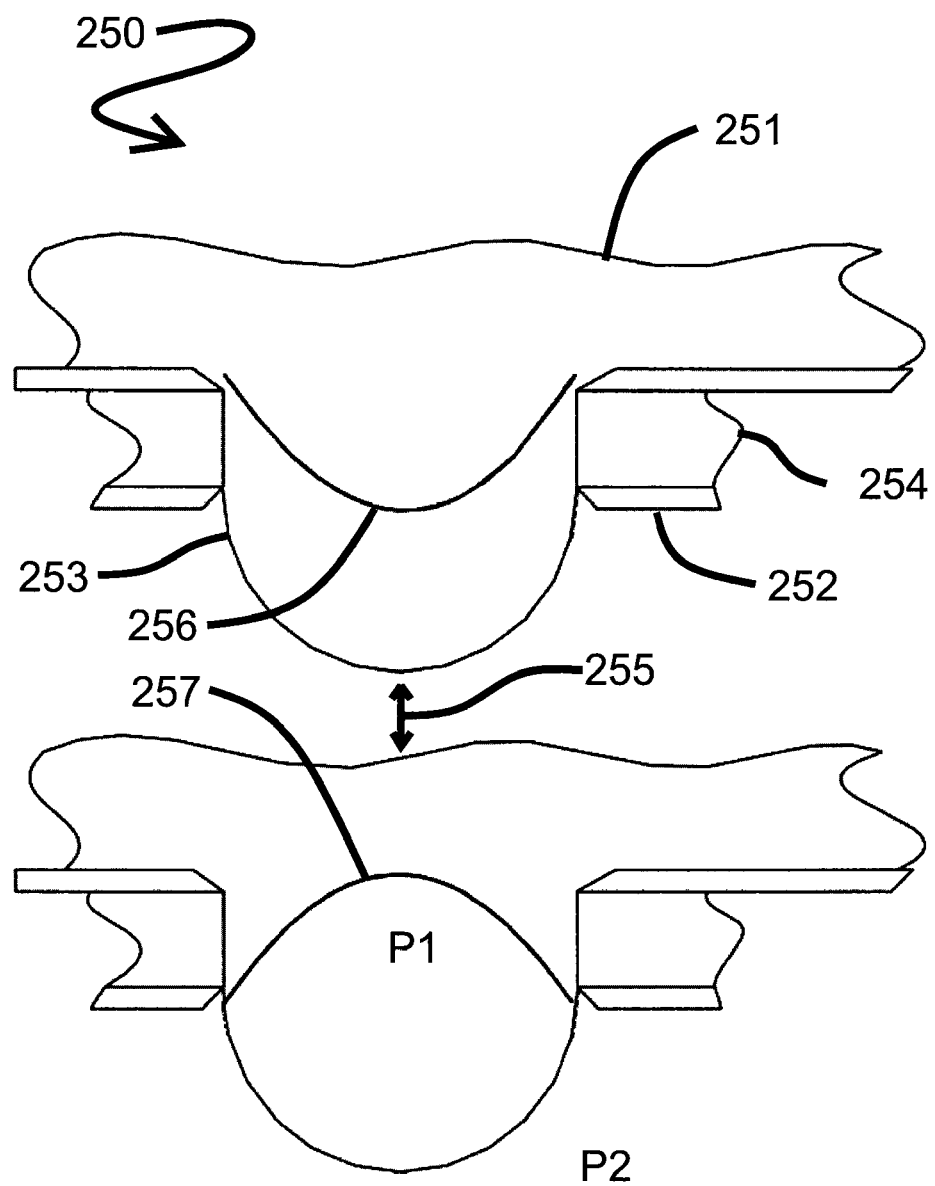
FIG. 24 depicts a resonant cutter device, according to an embodiment of the invention.

FIG. 24 illustrates a resonant cutter device 250. As in the above described devices, a tissue 251 is caused by suction to form a bulge 253 into the lumen of a tube. Insulating coating 252 allows current flow only through the bare metal edge of the orifice in metallic conductor 254. By applying an RF signal of appropriate frequency, the orifice can work as a resonant chamber for thermally generated acoustic waves. Graphs 256 and 257 show acoustic pressure vs. position in a circular orifice 180 degrees out of phase and the double headed arrow 255 indicating that the system is resonating between these two conditions. The maximum current density is at the surface of the metal so this is an antinode because maximum heating and volume expansion to drive acoustic waves occurs here. As the circular pressure wave (another name for the acoustic wave) travels radially inwards, the energy per unit length (i.e. power density) increases. At the center point of the circle will be very high energy density (not infinite because of damping, z-axis loss, and other loss mechanisms). If the wave has velocity V and the radius of the orifice is R then the wave will reach the center in R/V seconds. This should be ½ wavelength to have an antinode here. As an example if the velocity of sound in the tissue is 1000 m/s and the radius of the circular orifice is 0.0001 m, then the wave will travel ½ wavelength in 0.1 microseconds, or a full wavelength in 0.2 microseconds. This corresponds to an RF frequency of 1/0.0000002 sec, or 5 MHz. Having a pressure antinode at the center of the orifice adds mechanical acoustic pressure P1 within the tissue so that there is an even greater absolute difference relative to suction pressure P2 outside the tissue acting to sever the tissue. Other factors acting to add stress to sever the tissue are volume expansion due to electrical resistance, heating due to rotation of dipoles (at 5 MHz a 100 microsecond pulse will drive 500 rotations which dissipate as heat). If more dipole heating is desired, a higher RF frequency can be selected to drive higher order acoustic harmonics and drive more dipole rotations. Note that the speed of sound will change within the orifice as the material properties of the tissue changes due to heating, so the frequency of the applied RF may be slewed during the pulse. The slew rate and magnitude would be determined experimentally ahead of actual use, and then played back during use for a particular tool. To further emphasize dipole heating the rotational frequency for water molecules could be used, and the driving signal would be in the microwave region at about 2.45 GHz. Now a 100 microsecond pulse will drive 245,000 rotations of the molecules, which becomes heat.

Device Fabrication

A variety of different mechanisms can be used in fabricating the components of the device. For example, the components of the handpiece can be made by injection molding of plastic. The suction cup can be made by overmolding a suitable elastomer (e.g., silicone, or polyurethane) over the electrode and stem, which have been positioned in the mold, though other materials can be used as well. The suction cup is designed to be collapsible to a small cross section so that it can be inserted through a corneal incision (e.g., an incision of less than 2 to 3 mm in length) but then can rapidly return to its circular shape after deployment. The thinner the walls are, the stiffer (higher durometer) the material can be. The size for the suction cup can range from about 4.5 mm to about 7 mm in diameter, while the height would commonly range from about 0.5 mm to about 1.5 mm. The suction cup and overall device design and size ranges can vary to match the surgical procedure being conducted.

The cutting element can be made from various materials. The metallic components of the electrode can be made by electroforming of suitable metals such as nickel, gold, steel, copper, platinum, iridium, etc. Connections between the electrode and leads in the stem can be made by electroplating, or welding. Typically, for electrical cutting elements, the material for the cutting element is electrically conductive, and for mechanical cutting elements, the material is hard enough to pierce the membrane. For both electrical and mechanical cutting elements, the material is also generally elastic enough to return to its prior shape after being squeezed to get through the tissue incision, or soft enough to be pushed back into circular shape by the polymeric support ring and/or by the suction cup in which it is mounted. For example, for an electrical cutting element, the materials can include those made by photochemical etching, such as spring steel, stainless steel, titanium nickel alloy, graphite, nitinol (NiTi alloy "memory metal"), nickel, nickel-chrome alloy, tungsten, molybdenum, or any other material that will allow the element to return to its prior shape. Other materials for electrical cutting elements include electrically conductive elastomers, including elastomers (e.g., silicone or polyurethane) mixed with appropriately shaped conductive particles (e.g., silver, gold, graphite, or copper) that can establish contact with each other and continue to be in contact with each other for the duration of the electrical discharge. An additional example of a material for electrical cutting elements includes a compliant mesh of very fine wires (e.g., diameter of about 1 or 2 microns) that can be anchored in the elastomeric support ring to make the conductive element. As a further example, materials can be used for electrical cutting elements that are made by sputtering metal onto a polymeric support, such as high conductivity metals (e.g., gold, aluminum, copper, etc.), which can be used to make very thin (e.g., 1 micron) elements with resistance within the usable range (e.g., 1 to 10 ohms) deposited by RF plasma sputtering.

Materials used for mechanical cutting elements can include photochemically etched metal (e.g., stainless steel), or a relatively hard plastic (e.g., phenolic), among others. Discrete micro teeth could be etched from single crystal silicon. Photochemical etching can used to make cutting elements that have a thickness of, for example, 25 microns, or 12.5 microns, or 5 microns, and so forth.

The above description is included to illustrate the operation of the embodiments and is not meant to limit the scope of the invention. The scope of the invention is to be limited only by the following claims. From the above discussion, many variations will be apparent to one skilled in the relevant art that would yet be encompassed by the spirit and scope of the invention. As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

I claim:

1. A capsulotomy device for accessing a lens capsule through a cornea of an eye, the device comprising:
    a handpiece;
    a stem held by the handpiece;
    a cutting element mounted to the stem, the cutting element configured to be compressed for insertion into an anterior chamber of the eye through an incision in the cornea and configured to expand inside the anterior chamber of the eye into a cutting position on the lens capsule, the cutting element comprising:
        an insulating support;
        an inner conductive ring on an inside surface of the insulating support, the insulating support securing the inner conductive ring to the stem;
        an outer conductive ring on an outside surface the insulating support opposite the inside surface of the insulating support, the insulating support securing the outer conductive ring to the stem, the insulating support between the inner conductive ring and the outer conductive ring; and
        a distal bridge conductor secured to the insulating support and electrically connecting the inner conductive ring and the outer conductive ring over the insulating support, the insulating support between the inner conductive ring, the outer conductive ring, and the distal bridge conductor; and
    first and second electrical leads electrically connected to the inner and outer conductive rings.

2. The device of claim 1, further comprising a detachable compression mechanism attachable to the handpiece to compress the cutting element for insertion into the tip of the handpiece.

3. The device of claim 2, wherein the compression mechanism comprises compression elements along the sides of the cutting element, and wherein the compression mechanism further comprises a floor and a roof, wherein the floor is proximate to the bottom of the cutting element and the roof is proximate to the top of the cutting element when the cutting element is placed in the compression mechanism, the floor and roof configured to prevent the cutting element from deflecting out of a plane comprising the cutting element and the compression elements.

4. The device of claim 3, wherein the compression elements comprise slidable arms between the floor and the roof.

5. The device of claim 3, wherein the compression elements comprise fixed walls between the floor and the roof, the fixed walls tapered to a hole for removal of the cutting element from the compression mechanism into a tip of the handpiece of the device.

6. The device of claim 2, wherein the compression mechanism comprises latching beams that attach to detents in the handpiece.

7. The device of claim 6, wherein the handpiece comprises slidable chamber latch locks adjacent to the detents, the chamber latch locks configured to prevent deflection and detachment of the latching beams when the latch locks are slid forward toward the cutting element.

8. The device of claim 1, wherein the cutting element is an electrode, and the device comprises one or more electrical elements for delivering current to an electrical lead connected to the electrode to heat the electrode for excising a portion of tissue of the lens capsule.

9. The device of claim 1, wherein the cutting element is mounted to a suction cup.

10. The device of claim 9, wherein the suction cup further comprises a flared skirt extending from an edge of the suction cup for securing the suction cup against the lens capsule to form a vacuum seal.

11. The device of claim 9, wherein the suction cup further comprises a lens capsule removal element on the underside of the suction cup within a barrier formed by the cutting element.

12. The device of claim 11, wherein the lens capsule removal element is selected from the group consisting of: a second suction cup, a barb, and a hook.

13. The device of claim 1, wherein the distal bridge conductor electrically connects the inner and outer conductive rings at a distal point on the insulating support diametrically opposite from a proximal point on the insulating support where the first and second electrical leads are electrically connected to the inner and outer conductive rings.

14. The device of claim 1, wherein the first electrical lead is electrically connected to the outer conductive ring at a proximal point adjacent to the stem and the second electrical lead is electrically connected to the inner conductive ring at the proximal point adjacent to the stem.

15. The device of claim 1, further comprising a proximal bridge conductor secured to the insulating support opposite the distal bridge conductor, the proximal bridge conductor electrically connecting the inner conductive ring to at least one of the first and second electrical leads.

16. The device of claim 1, wherein the cutting element is configured to conduct current from the first electrical lead to the second electrical lead through the outer conductive ring, the bridge conductor, and the inner conductive ring.

17. The device of claim 16, wherein the distal bridge conductor is positioned such that half of the current is conducted around a first half of the outer conductive ring and half the current is conducted around a second half of the outer conductive ring.

18. The device of claim 16, wherein the distal bridge conductor is positioned such that half of the current is conducted around a first half of the inner conductive ring and half the current is conducted around a second half of the inner conductive ring.

19. The device of claim 1, wherein the distal bridge is disposed on a top surface of the insulating support, the top surface different from the inside surface and the outside surface.

20. A surgical device for cutting tissue, the device comprising:
    a handpiece;

a stem held by the handpiece;

a cutting element mounted to the stem, the cutting element configured to be compressed for insertion through an incision and configured to expand into a cutting position on the tissue, the cutting element comprising:
- an insulating support;
- an inner conductive ring on an inside surface of the insulating support, the insulating support securing the inner conductive ring to the stem;
- an outer conductive ring on an outside surface the insulating support opposite the inside surface of the insulating support, the insulating support securing the outer conductive ring to the stem, the insulating support between the inner conductive ring and the outer conductive ring; and
- a distal bridge conductor secured to the insulating support and electrically connecting the inner conductive ring and the outer conductive ring over the insulating support, the insulating support between the inner conductive ring, the outer conductive ring, and the distal bridge conductor; and first and second electrical leads electrically connected to the inner and outer conductive rings.

* * * * *